US009023818B2

(12) United States Patent
Christian

(10) Patent No.: US 9,023,818 B2
(45) Date of Patent: *May 5, 2015

(54) PHARMACEUTICAL AGENTS CONTAINING CARBOHYDRATE MOIETIES AND METHODS OF THEIR PREPARATION AND USE

(75) Inventor: Samuel T. Christian, Alabaster, AL (US)

(73) Assignee: Glycon LLC, Riverside, AL (US)

( * ) Notice: Subject to any disclaimer, the term of this patent is extended or adjusted under 35 U.S.C. 154(b) by 68 days.

This patent is subject to a terminal disclaimer.

(21) Appl. No.: 12/913,543

(22) Filed: Oct. 27, 2010

(65) Prior Publication Data

US 2011/0237544 A1  Sep. 29, 2011
US 2014/0057869 A9  Feb. 27, 2014

Related U.S. Application Data

(63) Continuation of application No. 11/343,266, filed on Jan. 30, 2006, now abandoned, which is a continuation of application No. 09/547,501, filed on Apr. 12, 2000, now abandoned.

(51) Int. Cl.
*A01N 43/04* (2006.01)
*A61K 31/70* (2006.01)
*C07H 5/06* (2006.01)
*A61K 31/7008* (2006.01)
*A61K 31/7052* (2006.01)

(52) U.S. Cl.
CPC ......... *A61K 31/7052* (2013.01); *A61K 31/7008* (2013.01)
USPC ............................................. 514/42; 536/29.1

(58) Field of Classification Search
CPC ... A61K 31/7034; A61K 31/7008; C07H 7/04
USPC ............................................. 514/42; 536/29.1
See application file for complete search history.

(56) References Cited

U.S. PATENT DOCUMENTS

| | | | |
|---|---|---|---|
| 3,929,813 A | 12/1975 | Bodor | 546/261 |
| 3,962,447 A | 6/1976 | Bodor | 424/263 |
| 4,032,676 A | 6/1977 | Heins et al. | |
| 4,190,672 A * | 2/1980 | Fahn | 514/566 |
| 5,380,837 A | 1/1995 | Nakada et al. | 536/17.9 |
| 5,639,737 A | 6/1997 | Rubin | 514/53 |
| 6,339,064 B1 | 1/2002 | McDevitt et al. | 514/42 |
| 6,548,484 B1 | 4/2003 | Christian | 514/25 |
| 2005/0250739 A1 | 11/2005 | Christian et al. | 514/620 |

FOREIGN PATENT DOCUMENTS

| | | |
|---|---|---|
| WO | WO 97/28174 | 8/1997 |
| WO | 9905089 | 2/1999 |
| WO | WO 01/97244 | 10/2007 |

OTHER PUBLICATIONS

Starkstein et. al., Journal of Neurology, Neurosurgery, and Psychiatry, 1996, British Medical Association, vol. 61, pp. 381-387.*
Walling et. al., Journal of Neuroscience Research, 1998, Wiley-Liss, vol. 54, pp. 301-308.*
Katsura et. al., Journal of Medicinal Chemistry, 1994, American Chemical Society, vol. 37, pp. 57-66.*
Walpole et. al., Journal of Medicinal Chemistry, 1993, American Chemical Society, vol. 36, pp. 2373-2380.*
Javit et al., "The American Journal of Psychiatry", American Psychiatric Association, 1994, vol. 151, No. 8, 1234-1236.
Moller et al., "Journal of Cerebral Blood Flow and Metabolism", Nature Publishing Group, 1998, vol. 18, 1184-1191 (1-10).
Sved et al., "Proceedings of the National Academy of Sciences of the United States of America", National Academy of Sciences, 1979, vol. 76, No. 7, 3511-3514.
Walton et al., "Analytical Biochemistry", Academic Press, 1987, vol. 164, 547-553.
Alexander et al., "Role of conjugation and red blood cells for inactivation of ciculating catecholamines," *Am. J. Physiol.* 247(1):R203-R207 (1984).
Alvarado et al., "Phlorizin as a competitive inhibitor of the active transport of sugars by hamster small intestine, in vitro," *Biochim. Biophys. Acta* 56:170-172 (1960).
Arita et al., "Studies on uptake of phenyl glycosides as inhibitors of D-glucose uptake by Rhesus monkey kidney cells," *J. Biochem.* 88:1399-1406 (1980).
Barnett et al., "Structural requirements for binding to the sugar transport system of the human erythrocyte," *Biochem. J.* 131:211-221 (1973).
Barnett et al., "Highlights of D1 dopamine receptor antagonist research," *Neurochem. Int.* 20 (Suppl.):119S-122S (1992).
Bencsics et al., "Dopamine, as well as, norepinephrine, is a link between noradrenergic nerve terminals and splenocytes," *Brain Res.* 761(2):236-243 (1997).
Berger et al., "Synthesis and receptor affinities of some conformationally restricted analogues of the dopamine D1 selective ligand (5R)-8-chloro-2,3,4,5-tetrahydro-3-methyl-5-phenyl-1 H-3-benzazepin-7-ol," *J. Med.* (1989).
Brewster et al., "trans-10,11-dihydroxy-5,6,7,8,12b-hexahydrobenzo[a]phen-anthridine: A highly potent selective dopamine D1 full agonist," *J. Med. Chem.* 33:1756-1764 (1990).
Bodor et al., "Elimination of a quaternary pyridinium salt delivered as its dihydropyridine," *J. Pharr. Sci*, 67(5):685 (1978).
Bodor, "Novel Approaches for the Design of Membrane Transport Properties of Drugs" In: "Design of Biopharmaceutical Properties Through Prodrugs and Analogs", Ed. E.B. Roche et al. APhA Academy of Pharmaceutical Sciences, Washington, D.C., p. 98-135 (1976).

(Continued)

*Primary Examiner* — Sarah Pihonak
(74) *Attorney, Agent, or Firm* — Kilpatrick Townsend & Stockton LLP

(57) ABSTRACT

Hydrophilic N-linked pharmaceutical compositions, methods of their preparation and use in neuraxial drug delivery comprising a glycosyl CNS acting prodrug compound covalently N-linked with a saccharide through an amide or an amine bond and a formulary consisting of an additive, a stabilizer, a carrier, a binder, a buffer, an excipient, an emollient, a disintegrant, a lubricating agent, an antimicrobial agent or a preservative, with the proviso that the saccharide moiety is not a cyclodextrin or a glucuronide.

2 Claims, No Drawings

(56) References Cited

OTHER PUBLICATIONS

Bodor et al., "Site-specific, sustained release of drugs to the brain," *Science* 214:1370-1372 (1981).
Bodor et al., "Redox delivery systems for brain-specific, sustained release of dopamine," *Science* 221:65-67 (1983).
Casagrande et al., "Synthesis and chemical properties of Ibopamine and of related esters of N-substituted dopamines:Synthesis of Ibopamine metabolites," *Arzneim.Forsch.* 36(2a):291-303 (1986).
Chen et al., "Transport-dependent accessibility of a cytoplasmic loop cysteine in human dopamine transporter" *J. Biol. Chem.* 275(3):1608-1614 (2000).
Choi et al., "Novel 3-aminomethyland 4-aminopiperidine analogues of 1[2-(diphenylmethoxy)ethy1]-4-(3-phenylpropyl)piperazines: Synthesis and evaluation as dopamine transporter ligands," *J. Med. Chem.* 43(2):205-213 (2000).
Clarkson et al., "Immortalized dpamine neurons: A model to study neurotoxicity and neuroprotection," *Proc. Soc. Exp. Biol. Med.* 222(2):157-163 (1999).
Claustre et al., "Conjugation and deamination of circulating dopamine: Relationship between sulfated and free dopamine in man," *J. Auton, Nerv. Syst.* 29(2):175-182 (1990).
Coffey et al., "[3H]WIN 35,428 binding to the dopamine uptake carrier. I. Effect of tonicity and buffer composition," *J. Neurosci. Methods* 51(1):23-30 (1994).
Czarnocki et al. "Enantioselective synthesis of (R)-(-)-Laudanosine and (R)-(-)-Glaucine from L-Ascorbic Acid," Tetrahedron: Assymetry, 7(9):2711-2720 (1996).
Dandrige et al. *J. Med. Chem.* 27:28 (1984).
Diez-Sampedro et al., "Galactose transport inhibition by cytochalasin E in rat intestine in vitro," *Can. J. Physiol. Pharmacol.* 77(2):96-101 (1999).
Duport et al., "An in vitro blood-brain barrier model: Cocultures between endothelial cells and organotypic brain slice cultures," *Proc. Natl. Acad. Sci. USA* 95(4):1840-1845(1998).
Earles et al., "Multisubstrate mechanism for the inward transport of dopamine by the human dopamine transporter expressed in HEK cells and its inhibition by cocaine," *Synapse* 33(3):230-238 (1999).
Fernandez et al., "Synthesis and biological studies of glycosyl dopamine deriviatives . . . ," Carbohyd. Res. 327:353-365 (2000).
Figlewicz, "Endocrine regulation of neurotransmitter transporters," *Epilepsy Res.* 37(3):203-210 (1999).
Findlay et al., "Inhibition of glycosidases by aldonolactones or corresponding configuration. 2. Inhibitors of b-N-acetylglucosaminidase," *Biochemical J.* 69:467-476 (1958).
Fischer et al., "5-Hydroxytraptamine stimulates glucose transport in cardiomyocytes via a monoamine oxidase-dependent reaction," *Biochem. J.* 311(2):575-583 (1995).
Fodor et al., *Acta Chim. Acad. Sci. Hung.* 28(4):409 (1961).
Freeman et al., "In: Chemical Regulation of Biological Mechanisms", Eds., Crieghton, A.M. and S. Turner. Royal Soc. Chemistry, London. pp. 154-165 (1982).
Gainetdinov et al., "Functional hyperdopaminergia in dopamine transporter knock-out mice," *Biol. Psychiatry* 46(3):303-311 (1999).
Gee et al., "Quercetin glucosides interact with the intestinal glucose transporter pathway," *Free Radic. Biol. Med.* 25(1):19-25 (1998).
Gerding et al., "Metabolism and disposition of the dopamine agonist 2-(N-propyl-N-2-thienylethylamino)-5_hydroxytetraline in conscious monkeys after subsequent iv, oral and ocular administration," *Drug. Metab. Dispos.* 18(6):923-928 (1990).
Geurts et al., "Assessment of striatal D1 and D2 dopamine receptor-G protein coupling by agonist-induced [35S]GTP gamma S binding," *Life Sci.* 65(16):1633-1645 (1999).
Giros et al., "Cloning and functional characterization of a cocaine-sensitive dopamine transporter," *FEBS Lett.* 295:149-154 (1991).
Giros et al., "Cloning, pharmacological characterization and chromosome assignment of the human dopamine transporter," *Mol. Pharmacol.* 42(3):383-390 (1992).

Glinsky et al. Inhibition of colony formation in agarose of metastatic human breast carcinoma and melanoma cells by synthetic glycoamine analogs Clin. Exp. Metastasis 14:253-267 (1996).
Green et al., "Glucuronidation of amines and hydroxylated xenobiotics and endobiotics catalyzed by expressed human UGT1.4 protein," *Drug Metab. Dispos.* 24(3):356-363 (1996).
Haspel et al., "Effects of barbiturates on facilitative glucose transporters are pharmacologically specific and isoform selective," *J. Membr. Biol.* 169(1):45-53 (1999).
Hibert et al., "Graphics coputer-aided mapping as a predictive tool for drug design: Development of potent, selective and stereospecific ligands for the 5-HT1A receptor," *J. Med. Chem.* 31:1087-1093 (1988).
Horton, Monosaccharide Amino Sugars. In: "The Amino Sugars": The Chemistry and Biology of Compounds Containing Amino Sugars. vol. 1A. Ed. R.W. Jeanloz. Academic Press. N.Y. pp. 4-18 (1969).
Hurtig, "Problems with current treatment of Parkinson's disease," *Exper. Neurol.* 144:10-16 (1997).
Husbands et al., "Structure-activity relationships at the monoamine transporters as sigma receptors for a novel series of 9-[3-(cis,5-dimethyl-l-piperazinyl)propyl] carbazole (rmicazole) analogues," *J. Med. Chem.* 42 (21): 4446-4455 (1999).
Hyson et al., "Calcium channel blockers modify jejunal uptake of D-galactose in rabbits," *Dig. Dis. Sci.* 41(9):1871-1875 (1996).
Hyson et al., "A high cholesterol diet blocks the effect of calcium channel blockers on the uptake of sugars in rabbit intestine," *Can. J. Phvsiol. Pharmacol.* 75(1):57-64 (1997).
Iorio et al., "Benzazepines structure-activity relationships between D1 receptor blockade and selected pharmacological effects," In: Neurobiology of Central D1 Dopamine Receptors, Eds., G.R. Breese and I. Creese, Plenum Press, NY. pp. 1-14 (1986).
Jaber et al., "Differential regulation of tyrosine hydroxylase in the basal ganglion of micre lacking the dopamine transporter," *Eur. J. Neurosci.* 11(10):3499-3511 (1999).
Jakas et al., "Syntheis and CNMR investigation of novel Amadori compounds (1-amino-1-deoxy-D-fructose derivatives) related to the opioid peptide, leucine-enkephalin," J. Chem. Soc., Perkin Trans. 2:789-794 (1996).
Jiang et al., "Dopaminergic properties and experimental anti-Parkinsonian effects . . . ," Clin. Neuropharmacol. 27(2):63-73 (2004).
Jones et al., "Dopamine neuronal transport kinetics and effects of amphetamine," *J. Neurochem.* 73(6):2406-2414 (1999).
Jork et al., "The influence of dopamine on the incorporation of different sugars into total proteins of hippocampal slices," *Pharmacol. Biochem. Behav.* 13(21):303-304 (1980).
Kaiser et al., *J. Med. Chem.* 25:697 (1982).
Kawasaki et al., "The identification of two N-acyldopamine glucosides in the left colleterial gland of the praying mantid, *Tenodera aridifolia sinensis* Saussure, and their role in the oothecal sclerotization insect," *Biochem.* 13:267-271 (1983).
Kerwin et al., "Negative ion electrospray mass spectrometry of polyphenols, catecholamines and their oxidation products," *J. Mass Sprectrom.* 31:1429-1439 (1996).
Kerwin, "Profiling peptide adducts of oxidized N-acetyldopamine by electrospray mass spectrometry," *Rapid Commun. Mass Sprectrom.* 11:557-566 (1997).
Kilboum et al., "Rapid and differentiallosses of in vivo dopamine transporter (DAT) and vesicular monoamine transporter (VMAT2) radioligand binding in MPTP-treated mice," *Synapse* 35(4):250-255 (2000).
Kitty et al., "Cloning and expression of a cocaine-sensitive rat dopamine transporter," Science 254(5031):578-579 (1991).
Knoerzer et al., "Dopaminergic benzo[a]phenanthridines: Resolution and pharmacological evaluation of the enantiomers of dihydrexidine, the full efficacy D1 dopamine receptor agonist," *J. Med. Chem.* 37:2453-2460 (1994).
Kuchel, "Peripheral dopamine in hypertension and associated conditions," *J. Hum. Hypertens.* 13(9):605-615 (1999).
Kuipers et al., 5-HT1A vs. D2-receptor selectivity of Flesinoxan and analogous N4-substituted and N1-arylpiperaimes, *J. Med. Chem.* 40:300-312 (1997).

(56) References Cited

OTHER PUBLICATIONS

Kumagai, "Glucose transport in brain and retina: Implications in the management and complications of diabetes," *Diabetes Metab. Res. Rev.* 15(4):261-273 (1999).

Leal et al., "The metabolism of CGS15873 in man using stable isotope pattern recognition techniques," *Biopharm. Drug Dispos.* 13(8):617-628 (1992).

Lichtenthaler, F.W. "Efficient Reaction Channels from Mono- and Disaccharides to Enantiopure Building Blocks and Exploitation of Their Application Profiles" In: Carbohydrates: Synthetic Methods and Applications in Medicinal Chemistry, edited by Ogura, H., Hasegawa, A., and Suami, T.Tokyo:Kodansha, p. 3-27 (1992).

Liljefors et al., "A molecular mechanics approach to the understanding of presynaptic selectivity for centrally acting dopamine receptor agonists of the phenylpiperidine series," *J. Med. Chem.* 29:1896 (1986).

Likhoshersfov et al., "Sythesis of N-chloroacetyl-β-glycopyranosylamines, derivatives of monosaccharides and lactose," *Russ. Chem. Bl.* 45:1760-1763 (1996).

Likhoshersfov et al., Russian Chemical Bulletin, 1998 47(6) p. 1214-1217 (abstract).

Lostao et al., "Presence of leptin receptors in rat small intestine and leptin effect on sugar absorption," *FEBS Lett.* 423(3):302-306 (1998).

Loland et al., "Defining proximity relationships in the tertiary structure of the dopamine transporter. Identification of a conserved glutamic acid third coordinate in the endogenous Zn2+ binding site," *J. Biol. Chem.* 274:36928-36934 (1999).

Maher et al., "Substrate specifically and kinetic parameters of GLUT3 . . . ," *Biochem. J.* 315:827-831 (1996).

Manzi et al., "In: Glycobiology: A Practical Approach," Eds. M. Fukuda and A. Kobata. IRL Press, Oxford University, Oxford. p. 29-31 (1993).

Martin et al., "Defects in Na+/glucose cotransporter (SGLT1) trafficking and function cause glucose-galactose malabsorption," *Nat. Genet.* 12(2):216-220 (1996).

Mathews et al. Biochemistry. Second Edition. The Benjamin/Cummings Publishing Company, Inc. p. 286 (1996).

Mattiuz et al., "Disposition and metabolism of olanzapine in mice, dogs and rhesus monkeys," *Drug Metab. Dispos.* 25(5):573-583 (1997).

McDermed et al., "Enantioselective binding of (+) and (-) 2-amiono-6,7-dihyroxy-1,2,3,4-tetrahydronaphythalenes and related agonists to dopamine receptors," In: Catecholamines: Basic and Clinical Fronteins, Eds., E. Usdin, I.J. Kopin and J. Barchas, Pergamon Press, NY. p. 568-570 (1978).

Meiergerd et al., "Striatal transporter for dopamine . . . ," *J. Neurochem.* 62(3):998-1008 (1994).

Melikian et al., "Membrane trafficking regulates the activity of the human dopamine transporter," *J. Neurosci.* 19(18):7699-7710 (1999).

The Merck Index: An Encyclopedia of Chemicals, Drugs, and Biologicals, 13th Edition 447 1 Maryadele J. O'Neil et al. Eds. 2001.

Meyer et al., "Pharmacokinetics and first clinical experiences with an antihypertensive dopamine (DA2) agonist," *Eur. Heart J.* 13(Suppl. D):121-128 (1992).

Mico et al., "Function-group metabolism of dopamine-2 agonists: Conversion of 4-(2-di-N-propylamnoethyl)-2-(3H)-indolone to 4-(2-di-N-propvlaminoethyl)-7-hydroxyl-2-(3H)-indolone," *J. Pharm. Sci.* 75(10):929-933 (1986).

Miller et al., "Dopamine transporters and neuronal injury," *Trends Phramacol. Sci.* 20(10): 424-429 (1999).

Minor et al., "Synthesis and molecular modeling of 1-phenyl-1,2,3,4-tetrahydroisoquinolines and related 5,6,8,9-tetrahydro-13bH-dibenzo[a,h]quinolizines as D1 dopamine antagonists," *J. Med. Chem.* 37:4317-4328 (1994).

Mizuma et al., "The beta-anomeric and glucose preferences of glucose transport carrier for intestinal active absorption of monosaccharide conjugates," *Biochim. Biophvs. Acta* 1200(2):117-122(1994).

Mizuma et al., "Intestinal active absorption of sugar-conjugated compounds by glucose transport system: Implications for improvement of poorly absorbable drugs," *Biochem. Pharmacol.* 43:2037-2039 (1992).

Mizuma et al., "Comparative study of active absorption by the intestine and disposition of anomers of sugar-conjugated compounds," *Biochem. Pharmacol.* 45(7):1520-1523 (1993).

Morgan et al., "N-b-Alanylnorepinephrine: Biosynthesis in insect cuticle and possible role in sclerotization," Insect Biochem. 17: 255-263 (1987).

Morgan et al., "Dopamine receptor subtypes and formalin test analgesia," *Pharmacol. Biochem. Behav.* 40(2):317-322 (1991).

Mueller et al., "1H and 13C NMR of 3-0 and 40 conjugates of dopamine and other catecholamines," *Bioconjug. Chem.* 4(1):47-53 (1993).

Navarro et al., "Effect of erythromycin on D-galactose absorption and sucrase activity in rabbit jejunum," *Can. J. Physiol. Pharmacol.* 71(3-4):191-194 (1993).

Ohnishi et al., "Blood-brain barrier transport of L-Tyrosine conjugates: a model study for the brain targeting using large neutral amino acid transport system," J. Drug. Targeting 8(6):395-401 (2000).

Ovalle et al., "Systematic analysis of oxidative degradation . . . ," Carbohyd. Res. 330:131-139 (2000).

Petersson et al., "Conformational analysis and structure-activity relationships of selective dopamine D1 receptor agonists and antagonists of the benzazepine series," *J. Med. Chem.* 33:2197-2204 (1990).

Pokorski et al., "Fatty acid acylation of dopamine in the carotid body," *Med. Hypothesis.* 50(2):131-133 (1998).

Pocchiari et al., "Ibopamine, an orally active dopamine-like drug: Metabolism and pharmacokinetics in rats," *Arzneim.-Forsch.* 36(2A):334-340 (1986).

Prakash et al., "Metabolism and excretion of a new anxiolytic drug candidate, CP-93,393, in healthy male volunteers," *Drug Metab. Dispos.* 26(5):448-456 (1998).

Prakash et al., "N-phenylalkyl-substitued tropane analogs of boat conformation of high selectivity for the dopamine versus serotonin transporter," *Bioorg. Med. Chem. Lett.* 9(23):3325-3328 (1999).

Ramaswamy et al., "1-0-acyl derivatives of glucose as non-penetrating inhibitors of glucose transport by hamster small intestine in vitro," *Biochim. Biophys. Acta* 443:284-287 (1976).

Rhoads et al., "Circadian periodicity of intestinal Na+/glucose cotransporter 1 mRNA levels is transcriptionally regulated," *J. Biol. Chem.* 273(16):9510-9516 (1998).

Riggs et al., "Specific dopamine D-1 and DA1 properties of 4-(mono- and dihydroxyphenyl)-1,2,3,4-tetrahydroisoquinoline and its tetrahydrothieno [2,3-c] pyridine analogue," *J. Med. Chem.* 30:1454-1458 (1987).

Roper et al., "NMR spectroscopy of N-(1-deoxy-D-fructos-1-YL)-L-amino acids (fructose-amino acids)," *Carb. Res.* 116:183-195 (1983).

Schauer, "In: Methods in Enzymology," Ed. V. Ginsberg. Academic Press, NY. p. 64-89 (1978).

Seiler et al., "Further characterization of structural requirements for agonists at the striatal dopamine D-1 receptor. Studies with a series of monohydroxyaminotetralins on dopamine-sensitive adenylate cyclase and comparison with dopamine receptor binding," *Mol. Pharmacol.* 22:281-289 (1982).

Seiler et al., "Characterization of dopamine receptor subtypes by comparative structure-activity relationships: dopaminomimetic activities . . . ," *J. Mol. Pharmacol.* 35:643-651 (1989).

Seiler et al., "Trans-Hexahydroindolo[4,3-ab]phenanthridines ("Benzergolines"), the first structural class of potent and selective D1 receptor agonists lacking a catechol group," *J. Med. Chem.* 34(1):3113-3117 (1991).

Shimada et al., Cloning and expression of a cocaine-sensitive dopamine transporter complementary DNA. *Science* 254(5031):576-578 (1991).

Shindo et al., "Metabolism of D- and L-isomers of 3,4 dihydroxyphenylalanine (DOPA). V. Mechanism of intestinal absorption of carbon-14 labeled D- and L-doba in rats," *Chem. Pharm. Bull.* 21(9):2031-2038 (1973).

(56) References Cited

OTHER PUBLICATIONS

Shah et al., "(+/−)-3-[4'-(N,N-dimethylamino)cinnamyl]benzazepine analogs: Novel dopamine D1 receptor antagonists," *J. Med. Chem.* 39:3423-3428 (1996).

Shukla et al., "Effect of desoxy-fructose derivatives of dopa and dopamine on body temperature," *Archiv für Arzneitherapie* 5(1):183-195 (1981).

Snyder et al., "Synthesis and evaluation of 6,7-dihydroxy-2,3,4,8,9,13b-hexahydro1H-benzo[6,7]cycloheptal [1,2,3ef][3]benzazepine, 6,7-dihydroxy-2,3,4,8,9,12b-hexahydroanthra-[10,4a,4-c,d]azepine and 10-(aminomethyl)- 9,10-dihydro-1,2-dihyroxyanthracene as conformationally restricted analogs of b-phenyldopamine," *J. Med Chem.* 38:2395-2409 (1995).

Storch et al., "HEK-293 cells expressing the human dopamine transporter are susceptible to low concentrations of 1-methyl-4-phenylpuridine acting via impairment of energy metabolism," *Neurochem. Int.* 35(5):393-403 (1999).

Sugamori et al., "A cognate dopamine transporter-like activity endogenously expressed in a COS-7 kidney derived cell line," *FEBS Lett.* 451(2):169-174 (1999).

Tamai et al., "Transporter-mediated permeation of drugs . . . ," *J. Pharm. Sci.* 89(11):1371-1388 (2000).

Takata et al., "Transport of glucose across the blood-tissue barriers," *Int. Rev. Cytology* 172:1-53 (1997).

Tarjanyi et al., "Chromatographic investigation and computer simulation of (-)deprenyl metabolism," New Approaches Chromatog. 243-266 (1993).

Umegae et al., *Anal. Chim. Acta* 208:59 (1988).

van de Waterbeemd et al., "Quantitative structure-activity relationships and eudismic analyses of the presynaptic dopaminergic . . . ," *J. Med. Chem.* 30:2175 (1987).

Vandenbergh et al., "A human dopamine transporter cDNA predicts reduced glycosylation, displays a novel repetitive element and provides racially-dimorphic TaqI RFLPs," *Brain Res. Mol. Brain Res.* 15(1-2):161-166 (1992).

Vannucci et al., "Glucose transporter expression in brain: Relationship to cerebral glucose utilization," *Dev. Neurosci.* 20(4-5):369-379 (1998).

Verhoeff et al., "Radiotracer imaging of dopaminergic transmission in neuropsychiatric disorders," *Psychopharmacol. (Berl)* 147(3):217-249 (1999).

Wang et al., "Conjugation patterns of endogenous plasma catecholamines in human and rat," *J. Lab. Clin. Med.* 101(1):141-151 (1983).

Wang et al., "Cathecholamine glucuronidation: An important metabolic pathway for dopamine in the rat," *J. Neurochem.* 40(5):1435-1440 (1983).

Weinstock et al., *Drugs Future* 10:645 (1985).

Whitfield et al., "Acceleration of sugar transport in avian erythrocytes by catecholamines," *J. Biol. Chem.* 249(13):4181-4188 (1974).

Wright et al., "Regulation of Na+/glucose cotransporters," *J. Exp. Biol.* 200(2):287-293 (1997).

Wu et al., "Molecular cloning of the mouse dopamine transporter and pharmacological comparison with the human homologue," *Gene* 233(1):163-170 (1999).

Wunder et al., "Enhanced albumin uptake by rat tumors," *Int. J. Oncol.* 11:497-507 (1997).

Doherty, "The synthesis of glyconyl peptides", Caplus abstract, J. Biol. Chem., vol. 201, 1953, pp. 857-866.

Haavik et al., "Tyrosine hydrolase adn Parkinson's disease", Mol. Neurobiol, vol. 16, No. 3, 1998, 285-309.

Woolley et al., "Synthesis of derivatives of 1,2-dichloro-4-benzensulfonamido-5-nitrobenzene and their use in the chemotherapy of spontaneious cancers," Canadian Journal of Chemistry, vol. 43, 1965, pp. 1454-1459.

U.S. Appl. No. 13/551,131, "Non-Final Office Action", mailed Oct. 22, 2014, 10 Pages.

Rao et al., "Parkinson's Disease: Diagnosis and Treatment", American Family Physician, vol. 74 No. 2, 2006, pp. 2046-2054.

Thomas et al., "Parkinson's Disease", Human Molecular Genetics, vol. 16 rev. iss. 2, 2007, pp. 2046-2054.

\* cited by examiner

PHARMACEUTICAL AGENTS CONTAINING CARBOHYDRATE MOIETIES AND METHODS OF THEIR PREPARATION AND USE

CROSS REFERENCE TO RELATED APPLICATIONS

The present application is a continuation of U.S. patent application Ser. No. 11/343,266, filed Jan. 30, 2006, which is abandoned and is a continuation of U.S. application Ser. No. 09/547,501 filed Apr. 12, 2000, which is abandoned and is hereby incorporated herein by reference in its entirety.

FIELD OF THE INVENTION

The invention relates generally to compositions and methods for treating peripheral and central neurological dysfunctions including e.g. infectious diseases, epilepsy, impaired motor dysfunction, schizophrenia, cognition, depression, behavior and mood disorders.

BACKGROUND OF THE INVENTION

It is estimated that mental disorders account for 10 percent of the global burden of disease with four disorders ranking among the 10 leading causes of disability worldwide: namely, unipolar major depression, bipolar disorder, schizophrenia and obsessive-compulsive disorder (National Institute of Mental Health, Report of the National Advisory Mental Health Council Behavioral Science Workgroup, March 2000). Unfortunately, the fundamental basis by which neurobiologic function translates into behaviors such as cognition, emotion, motivation, development, personality and social interaction are (at present) largely unknown.

Delivery of drugs from the blood and into neural tissues (neuraxial delivery) is a key aspect complicating clinical rehabilitation and intervention techniques. The blood brain barrier effectively limits access of many classes of known and potentially useful pharmaceutical agents. For instance, in Parkinson's disease it has long been understood that the disease results from a defect in dopamine biosynthesis, but it has proven exceptionally difficult to effect proper delivery of therapy across the blood brain barrier into affected nigrostriatal tissues. Catecholamines including dopamine, norepinephrine and epinephrine are produced by chromaffin cells in the adrenal medulla responding as a specialized ganglion to sympathetic enervation from preganglionic fibers of the splanchic nerve. However, catecholamines do not cross the blood-brain barrier, hence, the need for synthesis within the CNS. Although metabolic replacement therapy in Parkinson's might theoretically be effected with L-Dopa, the precursor of dopamine and a compound, which readily crosses the blood-brain barrier, the compound is highly unstable and rapidly inactivated in blood.

L-dopa, Levodopa, Cardiodopa (an inhibitor of dopa decarboxylase), Deprenyl (inhibiting dopamine degrading monoamine oxidase), Sinemet (a controlled release form of Levodopa) and their combinations and derivatives suffer from many major disadvantages common also in certain other drugs which might be used in neuraxial therapies, e.g. poor aqueous solubility, poor brain penetrability, relatively short half-lives, dosing fluctuations and numerous side effects. Observed side effects accompanying chronic use in Parkinson's patients include motor fluctuation, dysfunctions, peak-dose dyskinesia, requirements for frequent dosing, involuntary movements, psychosis, confusion, visual hallucinations, bradykinesia, rigidity, tremors, gastrointestinal and gentiourinary dyantonomia, hypotension and cognitive decline (Hurtig, 1997). Often after 3-5 years of treatment patients reportedly develop complex dose-related unpredictable response fluctuations leading to a progressive decrease in therapeutic efficacy and also possible onset of serious side effects such as abnormal involuntary movements, end-of-dose deterioration and abrupt near instantaneous on-off changes in patient disability. "Adaptation" by neural tissues to chronic administration is complex, and may include down-regulation of dopamine receptor expression as well as metabolic changes in post-striatal neurons. In addition to these neurologic side effects, metabolism of oral dopa compounds to dopamine in the stomach and gastrointestinal tract (even in the presence of decarboxylase inhibitors) can often lead to unwanted side effects including severe nausea and hypotension. Levodopa methyl and ethyl esters given orally suffer many of these same problems. Thus, all current therapies for treating Parkinsonism suffer from serious side effects, bioavailability problems, or both, and there has been a long-felt need for improved pharmaceutically active agents for metabolic replacement therapy in Parkinson's and related diseases (Hurtig, 1997).

In pharmacologic studies conducted over the past 20 years, the results seem to suggest relatively stringent structural requirements for activation of the D1 receptors, particularly in regard to any nitrogen atoms present in the compound (e.g., see Seiler et al., 1991; Berger et al., 1989; Brewster et al., 1990; Kaiser et al., 1982; Dandridge et al., 1984; Brewster et al. 1990; Weinstock et al., 1985; Riggs et al.; Seiler et al., 1982; Shah et al., 1996; Knoerzer et al., 1994). In addition, the nature of the terminal group (i.e., amino), or presence or length of an n-alkyl chain (Iorio et al., 1986) may reportedly influence binding interactions at D1 sites. Based on experience with different pharmacophores, several receptor models have been proposed (Seiler and Markstein, 1989; Petersson et. al., 1990; Brewster et. al., 1990; Knoerzer et. al., 1994; Snyder et. al., 1995; Minor et. al., 1994). By comparison, pharmacologic studies of D2-like receptors suggest somewhat less rigid overall structural requirements, but also restrictions around any nitrogen atoms (e.g., see McDermed et al. 1979; Freeman and McDermed, 1982; Liljefors et al., 1986; van de Waterbeemd et al., 1987).

The $Na^+/Cl^-$ dependent dopamine transporter, DAT1, granule system mediates calcium-dependent outward dopamine release into the synaptic cleft and inward energy-dependent dopamine vesicular re-uptake into the cytoplasm of presynaptic neurons. Loading of biosynthetic dopamine into granules is effected by the vesicular monoamine transporter (VMAT2; reviewed in Miller et al., 1999). DAT may also control movements of other monoamines in brain tissues. Cocaine, amphetamines, phencyclidine and certain anti-depressants and uptake inhibitors interfere with dopamine transport by DAT (e.g., see Jones et al., 1999; Giros et al., 1992). DAT function may be regulated by steroid hormones, has second order dependence on $Na^+$ (Earles et al., 1999) and may be coupled (or uncoupled) to modulatory second messenger systems, (e.g., down-regulation of DAT accompanying activation of protein kinase C by phorbol esters), and ionic currents (Melikian et al., 1999; reviewed in Figlewicz, 1999). Radiotracer imaging methods have been used to localize DAT (e.g., within the nucleus accumbens and mid-brain regions) and D1 and D2 receptors (e.g., in nigrostrial pathways) in the brains of normal subjects, as well as in patients with Parkinson's disease and neuropsychiatric diseases such as schizophrenia (reviewed in Verhoeff, 1999). Structure activity studies of antagonists have suggested that: (i) the DAT transporter may be sensitive to N-substitution (Choi et al., 2000); (ii) N-phenyl-substituted analogues may inhibit transport (Prakash et al., 1999; Husbands, et al., 1999); (iii) certain energetically unfavored boat conformations of rings may have high affinity for DAT (Prakash et al., 1999); (iv) structural rearrangement of the DAT protein may occur and be required for inward transport (Chen et al., 2000;); (v) the DAT protein contains an endogenous $Zn^{2+}$ binding site (Loland et al., 1999); (vi) DAT transporter function is sensitive to aromatic substitutions (Husbands, et al., 1999); and, (vii) apparent ordered kinetics for DAT transporter function is $Na^+$ binding first, then dopamine and then $Cl^-$.

Several tissue enzyme systems exist for altering catecholamines, including dopamine. Monoamine oxidases, MAO-A in neural tissues and MAO-B in other tissues including stomach and intestine, are oxioreductases that deaminate dopamine and other catecholamines with preferential activity manifest for 2-phenylethylamine and benzylamine. Catechol-O-methyltransferase is a cytosolic enzyme that catalyzes addition of a methyl group, usually at the 3 position of a benzyl ring. O-methoxylated derivatives may be further modified by conjugation with glucuronic acid. Non-neuronal dopamine transporter uptake mechanisms may also exist, e.g., in kidney (Sugamori et. al., 1999).

Oral delivery of drugs constitutes special chemical challenges, i.e., general simultaneous requirements for intestinal penetration, blood borne delivery, blood-brain-barrier penetrability and maintenance of functional (receptor binding and/or metabolic) utility. CNS active drugs constitute yet additional special and challenging problems, i.e., low pH stability (or protection) and intestinal transport. Intestinal intracellular transport mechanisms for amino acids, vitamins and sugars are varied. Glucose transport has recently been reviewed (Takata et. al., 1997). Transport mechanisms for glucose include intestinal transport vesicles and $Na^+$/glucose co-transporters (SGLTs), i.e., driving active transport of glucose and galactose across the intestinal brush border by harnessing $Na^+$ gradients across the cell membrane. Net rates of vesicle transport and exocytosis have been estimated to be in the range of 10 thousand to 1 million per second (Wright et. al., 1997). Missense mutations in SGLT1 reportedly result in potentially lethal inability to transport glucose and galactose (Martin et. al., 1996). Certain sugar specificity's, structural requirements and capabilities of $Na^+$-dependent glucose transport carriers have been investigated with impure receptor membrane preparations, and/or mixtures of receptors, with the findings that the glucosyl transporter in human erythrocytes (i.e., GLUT1): (i) seems to require that the ring oxygen atoms at positions C1, C3, C4, and possibly C6, be capable of forming hydrogen bonds with the transporter protein, and (ii) a hydrophobic group at C5 may increase affinity for the transporter (Barnett et al., 1973). Intestinal glucose transporter mechanisms reportedly prefer: (i) β-anomers to α-anomers; (ii) β-D-glucose to β-D-galactose; and, (iii) β-glucoside>α-glucoside>β-galactoside>α-galactoside. The α-anomers of glucose and galactose were reportedly hydrolyzed to their aglycone constituents during a non-$Na^+$-dependent desglucosylation transport (Mizuma et. al., 1992, 1993, 1994). Apparently unrelated studies of antiviral glycosides have reportedly found that: (i) C1 phenyl-substituted glycosides and para-substituted butyl-phenyl derivatives may inhibit glucose transporters (Arita et al., 1980); (ii) C1O-acyl glycoside derivatives with alkyl chains or carbonyl groups (as an aglycone substituent) may act as non-penetrating inhibitors of glucose transport (Ramaswamy et al., 1976); and (iii) 1-5-anhydroglucitol and 6-deoxyglucose may be transportable (Alvarado et al., 1960). Thus, like dopaminergic receptor binding, the art suggests that special chemical structural requirements may exist for intestinal transport.

Metabolic replacement therapy using compounds that are endogenously converted to dopamine, e.g., Levodopa, results in stimulation of both D1-like and D2-like dopaminergic families of receptors. While agonists are theoretically superior to Levodopa (i.e., because they should not be dependent on enzymatic conversion), in clinical use they have been shown to lack the therapeutic potency of Levodopa. Direct acting D2 agonists (e.g., bromocriptine, lisuride and pergolide) have also shown limited efficacy in monotherapy and are primarily used as add-on therapy to L-Dopa.

Dopamine administered intravenously, while not crossing the blood brain barrier, binds D1-like and D2-like dopamine receptors in the periphery and is reportedly useful in certain treatments for peripheral defects such as congestive heart failure and hypertension (e.g., Kuchel, 1999). However, it's utility is also limited by bioavailability problems. Thus, there has also been a long-standing need for improved dopaminergic catechol agonists with improved bioavailability and penetrability of myelinated nerves, i.e., for peripheral use in treatments of e.g. hypertension and congenital heart diseases.

Success in development of a candidate neuropharmaceutical agent may often turn on issues of whether receptor binding activity can be retained while optimizing for intestinal transport, pharmacologic half-life in blood and blood brain barrier penetrability. For example, pharmacologic studies conducted over at least the past 20 years, seem to suggest relatively stringent structural requirements for activation of D1 receptors, particularly in regard to any nitrogen atoms present in a compound (e.g., see Seiler et al., 1991;Berger et al., 1989; Brewster et al., 1990; Kaiser et al., 1982; Dandridge et al., 1984; Brewster et al. 1990; Weinstock et al., 1985; Riggs et al.; Seiler et al., 1982; Shah et al., 1996; Knoerzer et al., 1994). In addition, the nature of any terminal group (i.e., amino), or presence or length of an N-linked alkyl chain (Iorio et. al., 1986) may reportedly influence binding interactions at D1 sites. Based on experience with different pharmacophores, several receptor models have been proposed (Seiler and Markstein, 1989; Petersson et. al., 1990; Brewster et. al., 1990; Knoerzer et. al., 1994; Snyder et. al., 1995; Minor et. al., 1994). Thus, relatively stringent chemistry may be imposed upon a potential drug candidate by just the requirement for receptor binding at a single class of receptor.

Unfortunately, even within a class, receptors may be structurally (and functionally) heterogeneous. For example, molecular cloning studies have identified several different genes encoding dopamine receptors. D1-like receptors, recognized pharmacologically by the SCH23390 specific agonist, activate adenylate cyclase resulting in increased intracellular cAMP. Two gene products have been identified D1A and D1B, (also identified pharmacologically as D5). D1B/D5 appears responsible for SCH23390 specific agonist activity. D2-like dopamine receptors, recognized pharmacologically by spiperone and sulpride specific agonists, appear to be encoded by three genes with multiple possible splice variants expressed in different brain regions, i.e., D2S, D2L, D3 and D4. D2-like receptors do not appear adenylate cyclase-linked and may decrease intercellular cAMP levels.

Emerging understanding of the activities of neurologic mediators within the brain suggest that underlying dysfunctions may have behavioral manifestations. For example, D2-like receptors have been identified as potential targets for development of anti-psychotic agents and treatments for schizophrenia, based e.g., on antipsychotic effects of chlorpromazine but with resultant drug-induced Parkinson's symptoms and increased risk of tardive dyskinesia. Schizophrenia is (at present) believed to result from hyperactive dopaminergic transmission in the mesolimbic region of the brain. While antipsychotic drugs with fewer side-effects have been developed (e.g., haloperidol, fluphenazine, clozapine, olanzapine, risperidone), to date, no consensus antipsychotic dopaminergic antagonist pharmacologic or receptor profile has emerged and approaches under active consideration include: (i) combination approaches for blockade of D2-like and D1-like receptors as well as $5\text{-}HT_2$ and $\alpha_1$ adrenergic receptors, and (ii) selective approaches for blocking D2 subtypes, e.g., D3 and/or D4 or D2L/S and D4.

Unlike systemic treatments, neuraxial delivery of pharmaceutical agents may be complicated by endogenous mechanisms for recycling, scavenging and transporting neural mediators. For example, the $Na^+/Cl^-$ dependent dopamine transporter, DAT1, granule system mediates calcium-dependent outward dopamine release into the synaptic cleft and inward energy-dependent dopamine vesicular re-uptake into the cytoplasm of presynaptic neurons. Loading of biosynthetic dopamine into granules is effected by the vesicular monoamine transporter (VMAT2; reviewed in Miller et al., 1999). DAT may also control movements of other monoamines in brain tissues. (Non-neuronal dopamine transporter uptake mechanisms may also exist, e.g., in kidney see Sugamori et al., 1999). Cocaine, amphetamines, phencyclidine and certain anti-depressants and uptake inhibitors provide examples of side-effects which may be encountered when dopamine transporter activity is interrupted (e.g., see Jones et al., 1999; Giros et al., 1992). DAT function may also be regulated by steroid hormones and transporter function has second order dependence on $Na^+$ (Earles et al., 1999) and may be coupled (or uncoupled) to natural modulatory second messenger systems and ion channels, e.g., down-regulation accompanying activation of protein kinase C by phorbol esters (Melikian et al., 1999; reviewed in Figlewicz, 1999).

Pharmacological studies of DAT antagonists have suggested that, like the D1 receptor (supra), DAT transporters may be sensitive to N- and aromatic-ring substitutions with N-phenyl-substituted analogues inhibiting transport (Choi et al., 2000; Prakash et al., 1999; Husbands, et al., 1999). In addition, certain energetically unfavored boat conformations of rings may have relatively higher affinity for DAT (Prakash et al., 1999). Structural rearrangement of the DAT protein may be required for inward transport with loading being $Na^+$ first, then dopamine and then $Cl^-$ (Chen et al., 2000).

Tissue enzyme systems for altering and inactivating hydroxyl-substituted aromatic amines and amides include oxioreductases, methylases and glucuronic acid conjugating enzyme systems. Monoamine oxidases, (i.e., MAO-A in neural tissues and MAO-B in other tissues including stomach and intestine), are oxioreductases that deaminate dopamine and other catecholamines with preferential activity manifest for 2-phenylethylamine and benzylamine. Catechol-O-methyltransferase is a cytosolic enzyme that catalyzes addition of a methyl group, usually at the 3 position of a benzene ring. O-methoxylated derivatives may be further modified by conjugation with glucuronic acid. Glucuronidation of catecholamine drug metabolites, i.e., involving hepatic glucuronosyltransferase and enzyme systems in kidney and intestine, have been reported in mammals and in the rat, dopamine glucuronides are reportedly present in cerebrospinal fluid (Wang et al., 1983). Several drugs investigated for dopaminergic agonists and antagonist properties are apparently metabolized and/or excreted as glucuronides, e.g., SCH23390 (a Schering prototype D1 receptor antagonist; Barnett, et al., 1992), CGS15873 (a Ciba-Geigy dopamine agonist; Leal et al., 1992), Carmoxirole (a Merck dopamine agonist; Meyer et al., 1992), Olanzapine (a Lilly dopaminergic compound; Mattiuz et al. 1997) and CP-93,393 (a Pfizer anxiolytic drug candidate; Prakash et al., 1998). Within this general class of cyclic Parkinson's drugs, it has been suggested that glucuronidation may be the mechanism targeting urinary and biliary excretion of phenolic drugs, e.g., see Mico et al., 1986 (indolone agonists); see Gerding et al., 1990 (N-0437, a tetralin agonist); see Wang et al., 1983 (catecholamines); see Green et al., 1996 (hydroxylated and carboxylated phenolic compounds); see Pocchiari et al., 1986 (Ibopamine); and see Claustre et al., 1990 and Alexander et al., 1984 (dopamine). Shindo et al., 1973 reportedly studied absorption of L- and D-dopa in vitro in ligated rat intestinal loops and found active transport and metabolism to dopamine glucuronides.

Certain cellular mechanisms for transporting glucose are known. For instance, intestinal intracellular transport vesicles containing Na+/glucose co-transporters (SGLTs) are known to drive active transport of glucose and galactose across the intestinal brush border by harnessing Na+ gradients across the membrane. Net rates of vesicle transport and exocytosis have been estimated to be in the range of 10 thousand to 1 million per second (Wright et al., 1997). Pointing out the essential nature of this transport, missense mutations in SGLT1 result in a potentially lethal inability to transport glucose and galactose (Martin et al., 1996). Specificity's and capabilities of transport are subjects of active current investigation (Mizuma et al., 1994). Antioxidant flavonol compounds are present in certain foods as glycosides and one recent study suggests that quercetin glucosides, a class of flavonols, may be transported across the rat small intestine via a glucose co-transporter pathway (Gee et al., 1998). Intestinal mechanisms for fructose and possible lactose absorption are currently less well understood. Unlike intestinal transport mechanisms, neural glucose transport at the blood brain barrier is reportedly mediated by endothelial cells and the sodium-independent facilitative transporter GLUT1 (Kumagai et al., 1999). At neuronal cells, glucose transport is reportedly mediated predominantly by GLUT3 (Vannucci, S. J. et al., 1998). Neural tissue is almost entirely dependent on glucose transport for normal metabolic activity because tissue stores of glucose are low (relative to demand).

The blood brain barrier effectively limits neuraxial delivery of many pharmaceutically active compounds, including dopamine. Approaches disclosed for delivering drugs to the brain include the following: namely, (i) lipophilic addition and modification of hydrophilic drugs, (e.g., N-methylpyridinium-2-carbaldoxime chloride; 2-PA; U.S. Pat. Nos. 3,929, 813 and 3,962,447; Bodor et al, 1976, 1978 and 1981); (ii) linkage of prodrugs to biologically active compounds, (e.g., phenylethylamine coupled to nicotinic acid as modified to form N-methylnicotinic acid esters and amides, Bodor et al., 1981 and 1983; PCT/US83/00725; U.S. Pat. No. 4,540,564); (iii) derivatization of compounds to centrally acting amines (e.g., dihydropyridinium quaternary amine derivatives; PCT/US85/00236); (iv) caging compounds within glycosyl-, maltosyl-, diglucosyl- and dimaltosyl-derivatives of cyclodextrin (Bodor U.S. Pat. No. 5,017,566, issued May 21, 1991; Loftsson U.S. Pat. No. 5,324,718, issued Jun. 28, 1994 disclosing cyclodextrin complexes); and (v) enclosing compounds in cyclodextrin caged complexes (e.g., Yaksh et al., U.S. Pat. No. 5,180,716). However, these approaches suffer from various different disadvantages including poor pharmacokinetic half-life, poor neuraxial bioavailability, variable dosing and side effects.

Objects of the invention provide methods for neuraxial delivery of pharmaceutical agents as N-linked amine and amide glycoconjugates, including cyclic and heterocyclic prodrug compounds.

SUMMARY OF THE INVENTION

Methods are disclosed for preparing and using hydrophilic prodrug N-linked glycosyl-amine and glycosyl-amide compounds, including cyclic and heterocyclic compounds having good aqueous solubility and pharmacokinetic half-life in blood, but which are also transportable by saccharide transporters in the gastrointestinal tract and in endothelial cells at the blood brain barrier. Compounds produced according to the methods of the invention find a variety of uses in therapeutic methods for treating symptoms of neurologic dysfunction e.g., in infection (e.g., antibiotics and anti-viral agents), depression (e.g., stimulants), anxiety (e.g., depressants and relaxants), stress, neuromotor dysfunction, epilepsy (e.g., anti-convulsants and muscle relaxants), Parkinson's disease (e.g., dopamine precursors), vascular disease (e.g., hypo- and hypertensive agents), cancer (e.g., anti-cancer agents), hormone therapies (e.g., steroids), gastro-intestinal and urinary diseases (e.g., emetics and diuretics), as well as, in anesthesia, sedation, hypnosis and analgesia (e.g., narcotic and non-narcotic).

DETAILED DESCRIPTION OF THE PREFERRED EMBODIMENT

While it may be common in the pharmaceutical sciences to develop chemical models to refine specificity and selectivity of compounds, it is less common to develop models that simultaneously support the needs of two or more receptor-ligand interactions, or of intracellular transport mechanisms as well as receptor-ligand interactions. Perenteral agonist and antagonist agents for treating neurological dysfunction are known to depend for their pharmaceutical activity upon a complex interplay between receptor binding affinity, lipophilicity and blood-brain barrier penetrability. Precursors for use in metabolic replacement therapies require delivery at an intracellular site in a neuron in a relatively intact form. Gastrointestinal drug delivery involves problems of transport, metabolism, methylation, glucuronidation and toxicity. Most surprisingly, methods have been discovered which simultaneously solve the multiple aspects of these most complex problems.

Objects of the invention provide novel therapeutic prodrug agents and methods for treating diseases localized within the central nervous system (CNS) and also within myelinated and non-myelinated regions of the peripheral nervous system. In other objects the invention provides methods for producing hydrophilic amine and amide prodrug pharmaceutical agents N-linked through the amide, or amine, to a carbohydrate moiety, i.e., glycosyl-amine or glycosyl-amide compounds, respectively. In other objects, the invention provides methods for improving the aqueous solubility, and thereby improved bioavailability, of poorly soluble pharmaceutical agents allowing their use in pharmaceutical compositions at lower concentrations with greater efficacy. In other objects, the invention provides new uses for poorly soluble pharmaceutical agents occassioned by improved aqueous solubility and thereby bioavailability. In other objects, the invention provides new pharmaceutical compositions comprising pharmaceutical agents which were previously too poorly soluble to allow their inclusion in hydrophilic formulations. In other objects, the invention provides formulations of the subject N-linked glycoconjugate prodrug compounds for use in treatments of neurological dysfunctions. In other objects, the invention provides cyclic and heterocyclic amide and amine prodrug compounds having good aqueous solubility and pharmacokinetic half-life in blood. In other objects, the invention provides novel therapeutic prodrug agents and methods for treating diseases localized within the central nervous system (CNS) and also within myelinated and non-myelinated regions of the peripheral nervous system. In yet other objects, the invention provides methods for treating subjects in need thereof with N-linked prodrug pharmaceutical agents which are actively transported by endogenous saccharide transporters across the intestinal lumen, then passively through the blood and then via endothelial cell facilitative transport at the blood brain barrier into neuraxial spaces. In other objects, the invention provides methods for production and use of timed-release, subcutaneous and intradermal, intranasal, buccal, trouch and suppository N-linked glycosyl pharmaceutical agents having high aqueous solubility. In other objects, the invention provides treatment methods for achieving steady-state plasma concentrations in subjects in need thereof using N-linked glycosyl prodrug compounds of high aqueous solubility. In other objects, the invention provides novel therapeutic methods, not previously possible, occassioned by enhanced delivery and the hydrophilic properties imparted to poorly soluble pharmaceutical agents according to the methods of the invention.

According to certain objects, the invention provides methods for producing and using novel dopamine N-linked glycosyl derivatives and novel methods for treating Parkinson's and related disorders. In other objects, the invention provides methods for producing and using multi-dose novel dopamine prodrug compounds having relatively high aqueous solubility, e.g., up to 500 mg/ml. In certain other objects, the invention provides compositions, methods and uses for relatively high therapeutically effective unit doses of dopaminergic prodrug compounds in relatively small volumes. In still other objects, the invention provides therapeutic methods for delivery of dopaminergic amine and amide prodrug compounds lacking a reactive carboxylic acid, making co-administration of a decarboxylase or monoamine oxidase inhibitor unnecessary in a treatment of Parkinson's or a related disease. In other objects, the invention provides methods for promoting and upregulating intestinal and blood brain barrier transport of poorly aqueous soluble amine and amide containing pharmaceutical agents, i.e., possibly compensating for malabsorption, erratic gastrointestinal absorption, irregular gastric contractions, and the like in patients with Parkinson's and related diseases. In still other objects, the invention provides methods for upregulating dopamine-receptors function in a subject by using a dual function prodrug pharmaceutical agent containing a dopamine-functionality and a saccharide-transporter functionality. The instant methods find particular uses in advanced Parkinsonism where a limited number of functional nigrostriatal neurons may be available and possible glutamate-induced dyskinesia is evident (i.e., possibly mediated through N-methyl D-aspartyl receptor upregulation). In yet other objects, the invention provides methods for transcutaneous delivery of stable dopaminergic pharmaceutical compositions, i.e., not possible previously with many prior dopa compounds because of their chemical instability. In other objects, the invention provides therapeutic methods employing N-substituted compounds, which, unexpectedly, are transportable by dopamine transporters (DAT) in the brain. In other objects, the invention provides methods for using N-phenyl-derivatives that, unexpectedly, do not inhibit DAT. In other objects, the invention provides methods for using N-phenyl derivative DAT ligands that allow loading of $Na^+$ and $Cl^-$, and allow normal structural conformational changes in the DAT protein which accompany inward transport and do not down-regulate transporter function, e.g., by activating a protein kinase. In other objects, the invention provides methods for using compounds that are not modified by monoamine oxidases, catechol-O-methyltransferase or glucuronidation mechanisms operative in the intestine and stomach.

Although certain in vitro studies may have suggested that certain tyrosine-related compounds may stimulate glucose transport, and that certain sugars may increase dopamine receptor binding activity, Applicants do not believe it has been appreciated, until now, that a single chemical entity could effect these processes to promote its own transport and to promote its own receptor binding. For example, Fischer et al., 1995 reported that tryptamine, 5-OH-tryptamine and dopamine may elicit about a 3-5 fold increase in glucose transport with about 1.8- and 1.5-fold increases in the amount of cell surface GLUT1 and GLUT4 transporters, respectively. Whitfield et al., 1974 suggested that catecholamines, including dopamine, might stimulate carrier-mediated transport of 3-O-methylglucose and galactose in avian erythrocytes. Coffey et al., 1994 suggested that binding of a radiolabeled tropane to a rat striatal membrane dopamine receptors might be increased in the presence of sucrose, fructose and mannose, but not dextrose or N-methyl-D-glucosamine (Coffey, et al. 1994). However, these respective reports utilized separate dopaminergic and sugar chemical entities, not a single chemical entity, to achieve their measured results.

For purposes of organizing the following disclosure, as well as, improved understanding of the scope and breadth of the subject prodrug compounds which may be used according to the instant therapeutic methods, as well as their constituent structures the subject compounds are generally described by the structure of FORMULA I: as set forth below, "A-B-D-E"  Formula I wherein: each of "-" constitutes a single bond; the "A"-moiety constitutes a CNS-active drug; the "B"-moiety constitutes a "bridging" alkyl moiety; the "D"-moiety constitutes a nitrogen "linker" (i.e., an amine or amide); and, the "E"-moiety constitutes a saccharide, as disclosed further below. While certain preferred instant compounds according to FORMULA I are set forth below as representative examples (below), before addressing the specifics, the meanings of general terms relating to FORMULA I are provided as follows: namely, "Prodrug", and "drug derivative" or "prodrug derivative" is used interchangeably in reference to the "A-moiety", FORMULA I (supra), and intended to mean a CNS acting drug (supra), as well as drugs useful for treating a neurologic dysfunction (supra). Representative examples of the subject CNS acting drugs are provided above, and other drugs useful for treating neurologic dysfunctions are disclosed below, i.e., in TABLE A and TABLE B.

"Bridge", is used in reference to the B-moiety, of FORMULA I (supra), and intended to mean an optional group according to FORMULA II, below, (as depicted linked through single bonds to each of the A-moiety and the D-moiety, supra):

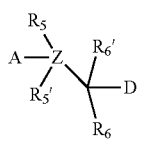

Formula II wherein,
Z is optional and when present comprises an optionally $R_5$-substituted lower alkyl; preferably, Z is absent or a lower alkyl comprising 1 or 2 carbon atoms; most preferably, Z is absent or a one carbon atom; and, $R_5$ and $R_{5'}$ (when present) and $R_6$ and $R_{6'}$ are groups selected from among hydrogen, hydroxyl, alkoxyl, carboxyl, alkoxylcarbonyl, aminocarbonyl, alkylamino-carbonyl or dialkylamino-carbonyl.

"Linker", is used in reference to the D-moiety, FORMULA I (supra), is intended to mean an optionally $R_7$-substituted amide or amine linking the B-moiety with the E-moiety, i.e., through each of two single bonds, according to FORMULA III, below (depicted linking the B- and E-moieties of FORMULA I): namely,

Formula III wherein, N comprises a nitrogen atom of a primary or secondary amine or an amide, preferably $R_7$ is a hydrogen or methyl, most preferably, $R_7$ is hydrogen.

"Saccharide", when used in reference to constituents "E-moiety" of FORMULA I (supra), is intended to mean a substituted or unsubstituted mono-, di-, tri- or oligosaccharide residue having e.g., constituent sugars comprising 3 carbon atoms (triose), 4 carbons (tetraose), 5 carbons (pentose), 6 carbons (hexose), 7 carbons (heptose), 8 carbons (octose) or 9 carbon atoms (nonose) such as may be present in interrelated straight chain, branched chain and cyclic forms, e.g., in a hexosyl straight chain, furanosyl 5-membered sugar ring, pyranosyl 6-membered sugar ring, and straight and branched oligosaccharide chains composed of monosaccharide sugar residues, as set forth further below.

"CNS acting prodrug", when used in regard to the "A" moiety of FORMULA I is intended to mean a pharmaceutical agent exerting an effect on a sympathetic or a parasympathetic nervous system. Representative examples include CNS-amines such as stimulants (e.g., phenethylamine, tyramine, MAO inhibitor cerebral stimulants and antidepressants, cerebral tricylic anti-depressants stimulants of the dibenzazepine type); neurotransmitters (e.g., dopamine); dopaminergic agents (e.g., Levodopa); precursors for use in a metabolic replacement therapy (e.g., L-Dopa); muscle relaxants; tranquilizers; anti-depressants (e.g., benzodiazepine and phenothiazine tranquilizers); mild and strong analgesics and narcotics; sedatives; hypnotics; narcotic antagonists; narcotic analgesics (e.g., methadone and meperidine); vascular agents (e.g., hypotensive β-blockers, anti-hypertensive agents, vasodilators); anesthetics; anti-epileptic and anti-convulsant drugs; hormones (e.g., steroid hormones, estrogens, progestins, hormones stimulating glucocorticoid production, sympathomimetic amines/cerebral stimulants and appetite suppressants); sympatholytic agents (e.g., as used in treatments of hypertension); centrally acting anti-cholinergic compounds; sympathetic stimulants (e.g., adrenergic agents); barbiturate antagonists; anti-infective agents (e.g., penicillins, tetracycline, cephalosporins); anticholinergic agents; tranquilizers; anticonvulsants; hypotensives/sympatholytics; ACE inhibitors; anti-epilepsy agents; neurotransmitters stimulating secretion of the pituitary hormones; hormones for inducing ovulation as well as for controlling fertility; antiviral agents (e.g., acyclovir), gonadotropin synthesis stimulants; diuretics; and emetics.

"N-linked glycosyl prodrug", when used herein in regard to a pharmaceutical agent, is intended to mean an "A"-moiety CNS acting prodrug compound linked through an amine or amide nitrogen to a saccharide E-moiety, according to FORMULA I, supra. Representative N-linked glycosyl prodrug compounds are also disclosed (below) and illustrated (see the EXAMPLES section, below), e.g., stimulants, precursors for use in a metabolic replacement therapy, neurotransmitter, muscle relaxants, tranquilizers, anti-depressants, analgesics, narcotics, sedatives, hypnotics, narcotic antagonists, narcotic analgesics, vascular-acting agents, hypotensives, sympatholytics, hypertensives, β-blockers, ACE inhibitors, anesthetics, anti-epileptic and anti-convulsant drugs, hormones, anti-cholinergic compounds, anti-cancer agents, pituitary hormone stimulants, gonadotropin stimulants, antibiotics, anti-viral agents, emetics, diuretics and the like.

"Saccharide" is intended to mean a mono-, di-, tri- or oligosaccharide made up of n sugar subunits linked to each other by glycosidic bonds, which subunits, when n is greater than 1, may be the same or different in respect to the localization of axial and equatorial ring substituents, number of carbon atoms and ring carbon locations and orientations of hydroxyl groups.

"Monosaccharide", when used in regard to the "E" moiety of FORMULA I, is used interchangeably with sugar to mean a sugar residue. Representative examples of sugar residues include the following: namely, polyhydroxy $C_1$ aldehydes (e.g. aldoses and ketoaldoses); polyols resulting from e.g., reduction of the $C_1$ aldehyde carbonyl to a hydroxyl (e.g., alditols and ketoses); polyhdyroxy acids resulting e.g., from oxidation of the $C_1$ aldehyde and/or the chain terminal hydroxyl (e.g., aldonic, ketoaldonic, aldaric and ketoaldaric); amino-sugars resulting from replacement of any hydroxyl in the chain with an amino group (e.g., aldosamines and ketosamines); aldehydro-acids resulting e.g. from oxidation of only the chain terminal hydroxyl in an aldehydro-sugar (e.g., uronic acids and keto-uronic acids); and their various lactones, i.e., cyclic esters of hydroxy carboxylic acids containing one 1-oxacycloalkan-2-one structure. The subject sugars may be straight chains and/or cyclic 3-, 4-, 5-, 6-, 7-, 8- and 9-membered sugar residues (e.g., hemiacetals and acetals) optionally substituted and linked with the pharmaceutical agent as set forth according to FORMULA I, supra. Representative triosyl residues include the aldoses D- and L-glyceraldehyde and derivatives thereof e.g., glyceraldehyde and glyceric acid phosphates; the keto-sugars D- and L-dihydroxyacetone and derivatives thereof. Representative tetraosyl residues include the aldoses D- and L-erythrose, threose, streptose and apiose; the keto-sugars D- and L-erythrulose; and derivatives thereof. Representative pentosyl residues include the D- and L-aldoses ribose, arabinose, xylose and lyxose; the D- and L-ketoses ribulose and xylulose; and, derivatives thereof. Representative hexosyl residues include aldosyl, furanosyl and pyranosyl sugars, e.g., cyclic and acyclic D- and L-aldoses such as allose, altrose, glucose, mannose, gulose, idose, galactose, talose, fructose, glucono-1,4-lactone, glucaro-1,4:6,3-dilactone, gluconofuranono-6,3-lactone; the ketoses ribo-hexylose, arabino-hexylolose, xylohexylose and lyxo-hexylose; and derivatives thereof. Representative 7-membered residues (i.e., heptosyl residues) include e.g., sedoheptulose and derivatives thereof; and, representative 9-membered residues (i.e., nonosyl residues) include N-acetylneuraminic acid and derivatives thereof. Also representative are, 2-deoxy-ribose, 6-deoxyglucose and 2-deoxyglucose, xyloascorbyllactone, digitoxose (2-deoxyaltromethylose), fucose (6-deoxy-galactose), gluconolactone, galaconolactone, rhamnose (6-deoxy-mannose), fructose (2-keto-arabohexose), aldaric acids, alditols, aldonic acids, ketoaldonic acids, and amino sugars; with the proviso that the sugar is not a cyclodextrin. Representative alditols includes e.g., erythritol, threitol, ribitol, arabinitol, xylitol, lyxitol, glucitol, allositol, altrositol, mannositol, gulositol, idositol, galactositol, talositol and their derivatives. Representative aldonic acids include erythronic acid, threonic acid, ribonic acid, arabinonic acid, xylonic acid, lyxonic acid, gluconic acid, allonic acid, altronic acid, mannonic acid, gulonic acid, idonic acid, galactonic acid, tolonic acid and their derivatives. Representative ketoaldonic acids include erythro-tetraulosonic acid, threo-tetraulosonic acid, ribopentulosonic acid, arabino-pentulosonic acid, xylo-pentulosonic acid, lyzo-pentulosonic acid, gluco-hexylosonic acid, allo-hexylosonic acid, altro-hexylosonic acid, manno-hexylosonic acid, gulo-hexylosonic acid, ido-hexylosonic acid, galacto-hexylosonic acid, talo-hexylosonic acid and their derivatives. Representative aldaric acids include erythraric acid, threaric acid, ribaric acid, arabinaric acid, xylaric acid, lyxaric acid, allaric acid, altraric acid, glucaric acid, mannaric acid, gularic acid, idaric acid, galactaric acid, talaric acid and their derivatives. Representative of amino sugar include erhtyrosamine, threosamine, ribosamine, arabinosamine, xylosamine, lyxosamine, allosamine, altrosamine, glucosamine, N-acetylglucosamine, N-methlglucosamine mannosamine, gulosamine, idosamine, galactosamine, talosamine and their derivatives. Representative uronic acids include erythrosuronic acid, threosuronic acid, ribosuronic acid, arabinosuronic acid, xylosuronic acid, lyxosuronic acid, allosuronic acid, altrosuronic acid, glucuronic acid, mannosuronic acid, gulosuronic acid, idosuronic acid, galactosuronic acid, talosuronic acid and their derivatives. Representative keto-uronic acids include keto-erythrosuronic acid, keto-threosuronic acid, keto-ribosuronic acid, keto-arabinosuronic acid, keto-xylosuronic acid, keto-lyxosuronic acid, keto-allosuronic acid, keto-altrosuronic acid, keto-glucuronic acid, keto-mannosuronic acid, keto-gulosuronic acid, keto-idosuronic acid, keto-galactosuronic acid, keto-talosuronic acid and their derivatives. Representative lactones include erythrolactone, threolactone, ribolactone, arabinolactone, xyloslactone, lyxoslactone, allolactone, altrolacone, glucolactone, mannolactone, gulolactone, idolactone, galactolactone, talolactone and their derivatives.

Preferred sugar residues for use according to the instant methods comprises aldose or ketose pentosyl or hexosyl sugars selected from the group consisting of D- and L-enantiomers of ribose, glucose, galactose, mannose, arabinose, allose, altrose, gulose, idose, talose and their substituted derivatives. Most preferably, the subject sugar comprises an aldose pentosyl or hexosyl sugar selected from ribose, glucose, galactose, glucosamine, galactosamine, N-acetylglucosamine, N-acetylgalactosamine, N-acetyl ribosamine, xylose, mannose and arabinose.

"Di-saccharide", when used in regard to the subject sugar residue, is intended to mean a polymeric assemblage of 2 sugar residues. Representative examples of disaccharides include homo-polymeric (e.g., maltose and cellobiose) and hetero-polymeric (e.g., lactose and sucrose) assemblages of sugars as set forth supra.

"Tri-saccharide", when used in regard to the subject sugar residue, is intended to mean a polymeric assemblage of 3 sugar residues, e.g., as set forth supra.

Preferably, the subject di- and tri-saccharide sugar moieties are metabolizable and/or acid hydrolyzable to mono- and di-saccharides transportable by saccharide transporters in mammals.

"Oligosaccharide", when used in relation to the subject E-moiety residue of FORMULA I, is intended to mean a polymeric assemblage of about 4 to about 10 glycosidically linked constituent homo-monosaccharide sugars (i.e., all the same constituent) or hetero-monosaccharide (i.e., different constituent) sugars. Each of the subject constituent sugars is linked one-to-another in a serial array through a series of glycosyl bonds formed between the $C_1$ and $C_4$ carbon atoms; or alternatively, between the $C_1$ and $C_3$ carbon atoms; or alternatively, between the $C_1$ and $C_6$ carbon atoms; with the proviso that when the sugar is according to FORMULA VIa, VIb, VIc or VId and comprises glycosidic linkage at $C_1$-$C_4$, then $R_8$ and $R_{11}$ are hydrogen, when linkage is at $C_1$-$C_3$, then $R_8$ and $R_{10}$ are hydrogen, and when linkage is at $C_1$-$C_6$, then $R_8$ and $R_{12}$ are hydrogen. The subject oligosaccharides may be homo-polymeric, i.e., all the same sugar constituent, or hetero-monosaccharide, i.e., different constituent sugars. Preferably, the subject oligosaccharide is selected from metabolizable and/or acid hydrolyzable oligosaccharides which following hydrolysis yield mono-, di- and tri-saccharides; and most preferably, the resultant constituent sugars are transportable by a saccharide transporter in a mammal. Representative oligosaccharides include lactose, maltose, isomaltose, sucrose, glycogen, cellobiose, fucosidolactose, lactulose, amylose, fructose, fructofuranose, scillabiose, panose, raffinose, amylopectin, hyaluronic acid, chondroitin sulfate, heparin, laminarin, lichenin and inulin. Preferably, the subject E-moiety, when present as an oligosaccharide, is selected from the group consisting of glucosyl and galactosyl homo- and heteropolymers. Most preferably, the subject E-moiety when present as an oligosaccharide, is selected from the group of metabolizable saccharides consisting of: (i) homopolymers such as an erythran, a threan, a riban, an arabinan, a xylan, a lyxan, an allan, an altran, a glucan (e.g. maltose, isomaltose, cellobiose), a mannan, a gulan, an idan, a galactan, a talan and their substituted derivatives; (ii) heteropolymers such as erythrosides, threosides, ribosides, arabinosides, xylosides, lyxosides, allosides, altrosides, glucosides (e.g., sucrose; (Glc-β1,4Frc), galactosides (e.g., lactose; Gal-β1,4-Glc), mannosides, gulosides, idosides, talosides and their substituted derivatives. Other representative oligosaccharides include the following: namely, sucrose, glycogen, fucosidolactose, lactulose, lactobionic acid, amylose, fructose, fructofuranose, scillabiose, panose, raffinose, amylopectin, hyaluronic acid, chondroitin sulfate, heparin, laminarin, lichenin and inulin. Preferably, the subject sugar, when present as an oligosaccharide, is selected from the group consisting of glucosyl and galactosyl homo- and heteropolymers, e.g., glucans, galactans, glucosides and galactosides. The subject sugar is not a cyclodextrin or derivative thereof. The subject E-moiety is not a cyclodextrin or derivative thereof.

"Aldose" is intended to mean a polyhydroxyaldehyde of the sugar of the general form $H[CH(OH)]_nC(=O)H$, wherein n is an integer greater than one; preferably, the subject aldose is in equilibrium with furanosyl and pyranosyl forms.

"Ketose", also known as ketoaldose, is intended to mean a sugar containing both an aldehydic group and a ketonic carbonyl group; preferably, the subject ketose is in equilibrium with intramolecular hemiacetal forms.

"Aldaric acid" is intended to mean a polyhydroxy dicarboxylic acid of a sugar having the general formula $HOC(=O)[CH(OH)]nC(=O)OH$, wherein n is greater than 1 and such as may be derived from an aldose by oxidation of both terminal carbon atoms to carboxyl groups.

"Alditol" is intended to mean an acyclic polyol having the general formula $HOCH_2[CH(OH)]_nCH_2OH$, wherein n is greater than one.

"Aldonic acid" is intended to mean a polyhydroxy acid having the general formula $HOCH_2[CH(OH)]_nC(=O)OH$, wherein n is greater than one and such as may be derived from an aldose by oxidation of the aldehyde function.

"Amino sugar" is intended to mean a sugar (defined supra) having one alcoholic OH group replaced by an amino group.

"Glycosyl" is intended to mean a hexose sugar substituent group; preferably, a glucosyl or galactosyl substituent.

"Glycosylamine", also known as N-glycosides, is intended to mean glycosyl group attached to an amino $—NR_2$ group; preferably, an N-linked glucosyl or galactosyl substituent.

"Furanose" is intended to mean a cyclic hemiacetal form of a sugar in which the ring is five membered.

"Pyranose" is intended to mean a cyclic hemiacetal form of a hexose sugar in which the ring is six membered.

As used herein the following additional terms are intended to have meaning as follows: namely, "Saccharide transporter" is intended to mean a cellular membrane protein capable of binding a saccharide and transporting that saccharide from one location to another on/in the cell. Representative examples of saccharide transporters include a glucose transporters (e.g., GLUT 1, 2, 3, 4 and 5), galactose transporters, a mannose transporters, fructose transporters, arabinose transporters and the like. Those skilled in the art are cognizant of methods by which test compounds may be shown capable of binding to a saccharide transporter, i.e., and examples of which are provided below.

"Pharmaceutical composition", is intended to mean a composition containing one or more N-linked glycosyl CNS-acting prodrug compounds according to FORMULA I and a formulary effective to provide a dosage form suitable for administration to man or domestic animals. Representative examples of formularies and dosage forms so suitable are provided below.

"Formulary" is intended to mean an agent added to a pharmaceutical composition comprising said hydrophilic N-linked CNS acting prodrug compound. Representative examples of formulary agents include additives, stabilizers, carriers, binders, buffers, excipients, emollient water-in-oil and oil-in-water emulsions, disintegrants, lubricating agents, antimicrobial agents, preservative and the like; as disclosed further below.

"Dosage form" is intended to mean a form of a pharmaceutical composition suitable for administration to a subject in need thereof. Representative dosage forms include solids and liquids, e.g., perenteral and injection solutions, powders and granules, emollient creams, syrups and elixirs, nasal and ophthalmic drops, intrabronchial inhalants, timed-release capsules, lozenges, troches, suppositories, dermal patches, impregnated bandages and the like.

"Treatment" is intended to mean a method of delivering to a subject in need thereof a pharmaceutical preparation with the aim of ameliorating or preventing one or more indicia of a central or peripheral neurologic dysfunction in the subject. The subject methods include delivering the preparation to a patient i) before the dysfunction has been diagnosed, (e.g., prophylactic protocols delivered with the aim of preventing development of the dysfunction), as well as, ii) after the dysfunction has been diagnosed, (e.g., therapeutic protocols). That the subject treatments have fulfilled the intended aim will be evident to a skilled practitioner by a change (increase or decrease) or complete elimination of one or more clinical indicia of disease.

"Indicia of dysfunction" is intended to mean a sign or symptom of disease as may be evident to a trained professional, e.g., a clinician or specialist, in view of patient performance, results in a standardized testing procedure, questionnaire, or in view of a combination of laboratory test results and observations.

"Neurologic dysfunction" is intended to mean a pathophysiologic or psychologic condition of a central or peripheral nervous system tissue, which condition is evidenced by a difference relative to a function of a nervous system activity in a normal healthy control subject. For example, the subject conditions include, but are not limited to, i) toxic dystrophy, (e.g., chemical or drug-induced secondary dystrophy in the nervous system), ii) vascular impairment e.g. resulting in damage to nervous tissues, iii) central nervous system degeneration or peripheral nerve degeneration, iv) nervous system lesions induced by physical trauma, v) nervous system complications of illnesses and infections (e.g., viral or bacterial); and vi) hereditary nervous system impairment. Representative illness, diseases, and conditions having neurologic dysfunction have been classified and codified ("International Classification of Diseases, Washington D.C., 1989).

"Subject in need thereof" is intended to mean a mammal, e.g., humans, domestic animals and livestock. Representative examples of subjects in need thereof include humans and domestic animals having a neurological dysfunction, e.g., a condition of hyper- or hypo-dopaminergic activity, such as may be evident in a patient with schizophrenia, Parkinson's disease, epilepsy, locomotor deficiency, hyperprolactinemia, Tourette's syndrome, Huntington's disease, psychosis, chronic psychiatric illness with amotivation, apathy, asociality, psychomotor adverse effects of drugs of abuse (e.g., cocaine, amphetamine, neuroleptics), subolivopontocerebellar atrophy (sOPCA), multiple system atrophy (MSA), bipolar disorder, chronic alcoholism, cocaine abuse, mood disorders, attention deficit disorder, physiologic stress, pesticide exposure (e.g., organochlorine insecticides), juvenile neuronal ceroid lipofuscinosis (JNCL), detached personality syndromes (as e.g. determined using the Karolinska Scales of Personality questionnaire) and the like. Representative examples of conditions exhibiting hyper-dopaminergic activity include schizophrenia, chronic psychiatric illness with hallucinations and delusions. Also representative are, patients with coronary hypertension, angina, ischemic myocardium and the like. In addition, prophylactic methods are envisaged for lowering aortic and pulmonary artery pressure during and after coronary bypass surgery and liver, kidney and heart transplant surgery. Vasodilation mediated by the instant compounds is without impairment of oxygen delivery or impairment of intrinsic neural or hormonal control systems.

"Metabolic replacement therapy" is intended to mean that the subject compound when administered to a subject in need thereof is capable of penetrating the blood brain barrier and partially or completely supplanting a medical need for a metabolic precursor in a subject in need thereof, e.g., a need for a catecholamine precursor in a patient with Parkinson's disease or a Parkinson's related disease. In certain embodiments, the compounds produced according to the instant methods, when administered according to the instant methods, effect transport into a neural cell and satisfy one or more metabolic requirements of catecholamine synthesis in that cell in a subject with a nigrostriatal dopamine insufficiency. Representative tests for determining that a test compound is so active are provided below, e.g., evidenced by increased tyrosine hydroxylase activity in a neural tissue.

"Ligand" as used herein refers to a compound that is capable of filling the three-dimensional space in a receptor binding site so that electrostatic repulsive forces are minimized, electrostatic attractive forces are maximized, and hydrophobic and hydrogen bonding forces are maximized.

"Parkinson's related disease", as used herein, is intended to mean a disease characterized by one or more symptoms which are also evidenced clinically in a patient with Parkinson's disease. Representative examples of symptoms evidenced in patients with Parkinsonism include seizure, loss of neuromotor control of muscle movements, tardive dyskinesia, Alzheimer's disease, Wilson's disease, post-encephalitic syndromes, Parkinsonism secondary to trauma and stroke, dementia, Lou Gehrig's disease, psychomotor retardation, schizophreniform behavior, anxiety and depression. Clinical features of Parkinson's related diseases are disclosed in Hurtig, 1997, incorporated herein by reference in its entirety.

"Intestinal cell" is intended to mean a columnar epithelial cell, e.g., a microvillus luminal cell, lining the small or large intestine, or lining the colon.

"Endothelial cell" is intended to mean a cell lining a blood vessel, e.g., a capillary cell or a cell of an artery or a vein.

"Neural cell" is intended to mean cells of the nervous system, including neurons, glial cells, Schwann cells and the like.

"Transportable in an intact form" is intended to mean that the subject N-linked glycosyl prodrug compound is not an inhibitor of a saccharide transporter, and is not substantially chemically altered during transport, e.g., it is not methylated or metabolized to an inactive form or converted to a glucuronide during transport, such that when the instant compound is transported from one side of a cell to the another side it remains substantially chemically and functionally unchanged.

"Neuraxial delivery" is intended to mean that administration of one or more of the instant pharmaceutical compositions, (comprising a CNS acting prodrug and a saccharide moiety as set forth supra), at one or more sites outside the central nervous system results in measurable levels of CNS acting prodrug within a neural tissue or a neural tissue fluid. Representative neural tissues include myelinated and non-myelinated nerves, brain and spinal cord. Representative neural tissue fluids include cerebrospinal fluid and tissue homogenates and expressates obtained from myelinated and non-myelinated nerves. Representative methods for measuring levels of CNS acting prodrugs are known to those of skill in the art.

"Substantially chemically unchanged" means that only conservative modifications of certain R group substituents of the A, B, D or E-moieties (FORMULA I, below) may occur during transport, e.g., removal of a halogen atom and replacement with a hydrogen, conversion of a hydroxyl to a methoxy and the like.

"Brain penetration index", abbreviated BPI, is intended to mean the mathematical ratio calculated as the amount of one or more of the instant compounds in brain tissue per gram of brain tissue, divided by the amount of the compound (or compounds) in liver tissue per gram liver tissue. The liver being chosen as a reference organ because of its intimate contact with blood and relative lack of barriers. Measurements of BPI may be made for instance at 5-60 minutes after administration of a test compound, e.g., by oral, subcutaneous or intravenous routes. The subject mathematical ratio is commonly expressed as a percentage, i.e., by multiplying the ratio by 100%. This procedure has the advantage that even for a sparingly soluble lipophilic drugs, (which tend to remain largely at an injection site with slow diffusion into the circulation), the amounts of drug in the liver will reflect the actual amount which is systemically available and not the initial dose injected. Certain of the preferred compounds according to the instant invention have BPIs in the range of about 2% to about 500%, most preferred compounds have a BPI of about 10% to about 200%.

"Microbial infection" is intended to mean infection of a mammalian host with a bacteria, virus, fungus, ricketssia, mycoplasma, prion agent, or parasite.

Embodiments of the invention provide pharmaceutical compositions containing a hydrophilic N-linked prodrug compound and a formulary, preferably in a dosage form as set forth defined supra. The subject N-linked prodrug compounds contain a CNS acting prodrug linked through an amine or amide bond with a saccharide moiety, preferably a mono-, di- or tri-saccharide. The instant pharmaceutical compositions are suitable for treating neurological dysfunction in a subject in need thereof without resort to combination therapy, e.g., a treatment with the instant compound an a monoamine oxidase or decarboxylase inhibitor. Despite N-linkage between the subject prodrug compound and the saccharide moiety, the compounds and compositions according to the invention when administered in an oral dosage form are substantially intact across the gastrointestinal lumen and into blood transportable (i.e., by endogenous active transport mechanisms); transportable in blood to the blood brain barrier (i.e., unassociated or associated with erythrocyte saccharide transporters); and, transportable across the blood brain barrier into myelinated and unmyelinated neural tissues (i.e., by facilitative transporters in endothelial cells). In certain preferred embodiments, the CNS acting prodrug compound comprises of a dopaminergic compound which, even when N-linked with saccharide, is still capable of binding both a dopamine receptor and a dopamine transporter.

In other embodiments, the invention provides methods and processes for preparing a variety of hydrophilic N-linked glycosyl prodrug compounds for neuraxial delivery, each of which methods and processes contains a synthetic step, or series of steps, which result in the formation of an amine or an amide bond between a saccharide moiety and a CNS acting prodrug compound.

In other embodiments, the invention provides processes for preparing pharmaceutical compositions comprising hydrophilic N-linked glycosyl prodrug compounds suitable for neuraxial delivery. The processes comprise the steps of first linking a CNS acting prodrug compound with a saccharide moiety through an amine or amide nitrogen atom. Representative conditions suitable for formation of amide or amine bonds between CNS acting prodrug compounds and saccharide moiety are illustrated in EXAMPLE 1, below. Next, formulary compounds (supra) are added to the resultant N-linked glycosyl prodrug to form the instant pharmaceutical composition. Representative formulary compounds, as disclosed supra, additives, stabilizers, carriers, binders, buffers, excipients, emollients, disintegrants, lubricating agents, antimicrobial agents, preservatives and the like.

In other embodiments, the invention provides methods for treating a subject in need thereof by the step of administering one or more of the instant pharmaceutical compositions comprising an N-linked glycosyl prodrug compound to the subject. Preferably, the instant methods involve treatment regimens useful for ameliorating one or more indicia of disease in a subject having a neurological dysfunction, as set forth supra. According to the instant disclosure, pharmaceutical compositions administered according to the instant method provide N-linked glycosyl CNS acting prodrug compounds which when released from the instant pharmaceutical compositions are transportable across the gastrointestinal tract, transportable in blood, and transportable across the blood brain barrier in a substantially intact form. Preferably, in the latter neuraxial sites, e.g., within tissue fluids or neural cells, the instant N-linked glycosyl prodrug compounds are activatable by an amidase, e.g., a glucosaminidase, a galactosaminidase and the like.

In yet other embodiments, the invention provides methods for improving the aqueous solubility and blood brain barrier penetrability of a prodrug compound by covalently linking that compound through an amine or amide bond to a saccharide. In certain preferred embodiments, the subject prodrug compound comprises a CNS acting prodrug and the instant methods are effective to both increase aqueous solubility and improve blood brain penetrability. While it may be common in the art to add hydrocarbon chains to prodrug compounds to increase lipid solubility, (i.e., often at the expense of decreased aqueous solubility), the instant methods provide an alternative, which simultaneously offers advantages of high aqueous solubility and good blood brain barrier penetrability.

In certain presently preferred embodiments, the invention provides methods for administering a metabolic replacement therapy to a subject in need thereof. The instant method involves administering to the subject one or more of the instant pharmaceutical preparations consisting of an N-linked glycosyl prodrug compound, with the requirement that the compound, when so administered, is capable of acting as a metabolic precursor in a cellular biosynthetic process. Representative examples of N-linked glycosyl CNS acting prodrug compounds for neuraxial delivery and metabolic replacement therapy are provided in the EXAMPLES section below.

In other embodiments, the invention provides methods for producing a variety of different prodrug compositions with improved bioavailability, CNS penetrability and adsorption enhancing activity. The methods involve the step (or steps) of linking a saccharide through an amide or amine bond with a prodrug compound.

In certain presently preferred embodiments, the invention provides improved methods for treating Parkinson's disease and symptomatically related diseases. The instant methods employ N-linked glycosyl prodrug compounds (supra) having improved bioavailability and aqueous solubility and fewer side effects.

In certain other preferred embodiments, the invention provides pharmaceutical compositions containing N-linked glycosyl dopaminergic prodrug compounds according to FORMULA I that are effective to produce a sympathomimetic response at a site of action at lower dosages than L-Dopa and in a more controlled manner.

In yet other embodiments, the invention provides dopaminergic pharmaceutical compositions with improved aqueous solubility and transportability by saccharide transporters and methods for their use in neuraxial delivery of metabolic replacement therapy across the intestine (e.g., in timed release dosage forms) and rectum (e.g., in suppositories).

Unlike dopamine, presently preferred embodiments of the invention provide CNS-acting dopaminergic prodrug compositions that offer advantages of possible decreased tissue ulceration, irritation and toxicity when injected or applied locally (e.g., onto a skin or mucosal surface).

The instant methods of the invention are particularly useful for improving the properties of a variety of sparingly water-soluble prodrugs that may have undesirable toxicological or pharmacokinetic profiles. Representative classes of pharmaceutical drug compounds that may contain sparingly water soluble, lipophilic and/or water-labile drugs which may prove suitable for use according to the instant methods are disclosed in TABLE A and TABLE B on the following pages. Representative pharmaceutical drug compounds contemplated for improvement according to the instant methods include those set forth in TABLE A, on the pages which follow, as well as derivatives thereof, with the presently preferred drug compounds disclosed in TABLE B, below (i.e., with chemical structures).

TABLE A

| Class of Agent: | Representative Examples: |
|---|---|
| Antineoplastic Agents | chlorambucil, lomustine, melphalan, methotrexate, hexamethylmelamine, teniposide, etoposide, semustine (methyl CCNU), fazarabine (Ara-AC), mercaptopurine, tubulazole, carmofur, carmustine, amsacrine, bruceantin, diaziquone, dideminin B, echinomycin, PCNU, mitoxantrone, podophyllotoxin derivatives (etopside, teniposide), doxorubicin, daunamycin, cyclophosphamide, tamoxifen, chlorambucil, melphalan, nitrogen mustard-type, methotrexate, aminopterin platinum coordination complexes, cisplatin, dactinomycin, mitomycin C, thioguanine, vincristine, vinblastine, alkaloids; hydroxyurea, DON, urea derivatives, 5FU, Ara-AC, pentostatin (2'-deoxycoformycin), Ara-C (cytarabine), 3-deazaguanine, dihydro-5-azacytidine, tiazofurin, sangivamycin, Ara-A (vitarabine), 6-MMPR, PCNU, FENU, HENU, nitrosoureas, spiromustine, bisbenzimidazole, L-alanosine (6-diazo-5-oxo-L-norleucine), DON, L-ICRF, trimethyl TMM, 5-methyltetrahydrohomofolic acid, glyoxylic, acid sulfonylhydrazone, DACH, SR-2555, SR-2508, desmethylmisonidazole, mitoxantrone, menogaril, aclacinomycin A, phyllanthoside, bactobolin, aphidocolin, homoharringtonine, levonantradol, acivicin, streptozotocin, hydroxyurea, chlorambucil, cyclophosphamide, uracil mustard, melphalan, 5-FU (5-fluorouracil), 5-FUDR (floxuridine), vincristine, vinblastine, cytosine arabinoside, 6-mercaptopurine, thioguanine, 5-azacytidine, methotrexate, adriamycin (doxorubicin), daunomycin (daunorubicin), largomycine polypeptide, aminopterin, dactinomycin, mitomycin C, podophyllotoxin derivatives, etoposide (VP-16), teniposide |
| Anti-inflammatory Agents (steroidal and non-steroidal) | dexamethasone, hydrocortisone, prednisolone, piroxicam, flurbiprofen, betamethasone, fludrocortisone, cortisone, triamcinolone, prednisone, aspirin, ibuprofen, indomethacin, sulindac, desoxycorticosterone, flumethasone, fluprednisolone, meprednisone, methyl prednisolone, prednisolone, triamcinolone, cortodoxone, flurandrenolone acetonide (flurandrenolide), paramethasone |
| Estrogens | 17β-estradiol, 17β-ethynylestradiol, ethynylestradiol 3-methyl ether, estriol, estradiol, estrone, 17α-ethynylestradiol (ethinylestradiol), mestranol, quinestrol |
| Androgens | 17-methyltestosterone, testosterone |
| Progestins | norethindrone, norethindrone, norgestrel, ethisterone, medroxyprogesterone acetate, progesterone, dimethisterone, norethindrone, norethynodrel, allylestrenol, cingestol, ethynerone, lynestrenol, norgesterone, norvinisterone, ethynodiol, oxogestone, tigestol |
| Antihistaminic Agents | benzimidazoles, astemizole, piperidines, levocabastine, piperazines, flunarizine, oxatomide, cinnarizine |
| Anticonvulsants, Barbiturates | phenytoin (diphenylhydantoin), ethotoin, phenobarbital, aminoglutethimide, carbamazepine, pentobarbital, phenobarbital, secobarbital |
| Vitamins | retinol (vitamin A), vitamin A-acetate, cholecalciferol and retinal, as well as other fat-soluble vitamins such as the E, D and K vitamins |
| Emetics and Anti-emetics | apomorphine, dimenhydrinate |
| Gastrointestinal Agents | piperidine derivatives such as loperamide and cisapride |
| Diuretics | chlorthalidone, furosemide and spironolactone, sulfonamide-type diuretics, aldosterone antagonist-type diuretics |
| Anticoagulants | dicumarol |
| Cardiotonics | digoxin and digitoxin |
| Androgens | 17-methyltestosterone, testosterone |
| Hypnotics and anesthetics | alfaxalone, etomidate, lidocaine |
| Antidepressants | sulpiride, desipramine, nortriptyline, octriptyline, maprotiline, opipramol and protriptyline, clonidine, methyldopa |
| Monoamine oxidase inhibitors | tranylcypromine |
| Antiviral Compounds | vidarabine, virazole (also known as ribavirin), acyclovir, amantadine, diarylamidines, 5-amidino-2-(5-amidino-2-benzofuranyl)indole, 4',6-diimidazolino-2-phenylbenzo(b)thiophene, 2-aminooxazoles, 2-guanidino-4,5-di-n-propyloxazole, 2-guanidino-4,5-diphenyloxazole, benzimidazole analogues, 6[[(hydroxyimino)phenyl]methyl]-1-[(1-methylethyl)sulfonyl]-1H-benzimidazol-2-amine; C-nucleosides, 5,7-dimethyl-2-β-D-ribofuranosyl-s-triazole(1,5-a)pyrimidine, (S)-9-(2,3-dihydroxypropyl)adenine, tiazofurin, selenazofurin, 3-deazauridine, 3-deazaguanosine, DHPG, 6-azauridine; idoxuridine, trifluridine (trifluorothymidine), BDVU (bisdihydroxyvinyluridine), zidovudine (AZT); dideoxycytidine; and 5,6-dichloro-1-β-D-ribofuranosylbenzimidazole, Ara-AC, pentostatin, Ara-C, dihydro-5-azacytidine, tiazofurin, sangivamycin, Ara-A, 6-MMPR, |

TABLE A-continued

| Class of Agent: | Representative Examples: |
| --- | --- |
| | desmethylmisonidazole, 5-FUDR, cytosine arabinoside, 5-azacytidine, ribavirin, acyclovir, (S)-9-(2,3-dihydroxypropyl)adenine, 6-azauridine, 5,6-dichloro-1-β-D-ribofuranosylbenzimidazole, 5,7-dimethyl-2-β-D-ribofuranosyl-s-triazole(1,5-a)pyrimidine, zidovudine (AZT), dideoxycytidine, dideoxyadenosine, dideoxyinosine, DHPG |
| Antimicrobial Agents | ampicillin, penicillin G, ketoconazole, itraconazole, metronidazole, miconazole, co-trimoxazole, amoxicillin, oxacillin, carbenicillin, benzylpenicillin, phenoxymethylpenicillin, methicillin, nafcillin, ticarcillin, bacampicillin, epicillin, hetacillin, pivampacillin, the methoxymethyl ester of hetacillin, ampicillin, chlortetracycline, demeclocycline, minocycline, doxycycline, oxytetracycline, tetracycline, methacycline, clindamycin, lincomycin, nalidixic acid, oxolinic acid, phenazopyridine, dicloxacillin, cephalothin, cephalexin, cefazolin, cefoxitin, moxalactam, ceforanide, cefroxadine, cephapirin, imidazole-type antifungal agents, econazole, clotrimazole, oxiconazole, bifonazole, metronidazole (metronidazole benzoate), fenticonazole, miconazole, sulconazole, tioconazole, isoconazole, butoconazole, ketoconazole, doconazole, parconazole, orconazole, valconazole and lombazole, trizole-type antifungal agents, terconazole, itraconazole, co-trimoxazole, sulfadiazine, sulfonamide |
| Antiprotozoal Agents | imidazole-type antiprotozoals, metronidazole, ornidazole, carnidazole, ipronidazole, tinidazole, nimorazole, benzimidazole-type antifungals, flubendazole |
| Antihelminthic Agents | benzimidazole-type, thiabendazole, oxibendazole, cambendazole, fenbendazole, flubendazole, albendazole, oxfendazole |
| Vasodilators | nitroglycerin, flunarizine, lidoflazine, mioflazine, dipyridamole, nifedipine |
| Anti-hypertensive Agents; Hypertensive Agents, β-Blockers | prizidilol, hydralazine, tracazolate, bethanidine, guanethidine, captopril, propranolol, atenolol, nadolol, timolol, metoprolol, clonidine, methyldopa, bethanidine, debrisoquin, hydralazine, and guanethidine and its analogues |
| $H_2$ Antagonists | imidazole-type, burimamide, metiamide, cimetidine, oxmetidine, famotidine |
| Serotonin Antagonists | piperidine-type, ketanserin, ritanserin, altanserin, piperazine-type, mianserin |
| Carbonic anhydrase inhibitors | acetazolamide, chlorzolamide, ethoxzolamine, methazolamide, L-671, 152, MK-927 |
| Hypoglycemic Agents | acetohexamide |
| Catecholamines and Dopaminergic Agents | L-DOPA, Dopamine, progabide, GABA, norepinephrine, epinephrine; serotonin, histamine, tryptamine |
| Adrenergic Agents | norepinephrine, epinephrine |
| Alzheimer's Agents | THA |
| Tranquilizers, Muscle relaxants | benzodiazepines such as chlordiazepoxide, diazepam, medazepam, oxazepam and lorazepam; phenothiazines such as carphenazine, fluphenazine, acetophenazine, carphenazine, fluphenazine, perphenazine, piperacetazine; benzoctamine; chlordiazepoxide, clorazepate; nitrazepam, temazepam; haloperidol, clopenthixol, haloperidol, clopenthixol; hydroxyzine; flurazepam, bromazepam, demoxepam, lorazepam, flurazepam, bromazepam, chlorazepate, nitrazepam and temazepam; hydantoin-type tranquilizers/anticonvulsants, phenytoin, ethotoin, mephenytoin; phenothiazine-type tranquilizers, acetophenazine, carphenazine, fluphenazine, perphenazine and piperacetazine |
| Benzodiazepine Antagonists | ethyl-β-carboline-3-carboxylate |
| Prostaglandins | $PGE_1$, $PGE_2$, $PGI_2$ |
| Anticonvulsants | hydantoins such as phenytoin, ethotoin, valproic acid, 5-hydroxy-2-n-propylpentanoic acid, 4-hydroxy-2-n-propylpentanoic acid, 3-hydroxy-2-n-propylpentanoic acid, valpromide |
| Narcotic Analgesics, Sedatives, Hypnotics | etryptamine, a cerebral stimulant; codeine, oxycodone, pentazocine, anileridine, hydromorphone, morphine and oxymorphone, noracymethadol, piminodine, pholcodine, ethinyl estradiol and mestranol, estrogens; meptazinol, cyclazocine, phenazocine, profadol, metopon, drocode, myfadol, levorphanol, ibuprofen, naproxen, flurbiprofen, zomepirac, sulindac, indomethacin, fenbufen, fenoprofen, indoproxen, ketoprofen, fluprofen, bucloxic acid, tolmetin, alclofenac, fenclozic acid, ibufenac, flufenisal, pirprofen, flufenamic acid, mefenamic acid, clonixeril, clonixin, meclofenamic acid, flunixin, diclofenac, carprofen, etodolac, fendosal, prodolic acid, sermetacin, indoxole, tetrydamine, diflunisal, naproxol, piroxicam, metazamide, flutiazin, tesicam. |
| Narcotic antagonists | nalorphine, naloxone, buprenorphine, nalbuphine, butorphanol, levallorphan, naltrexone, nalmefene, alazocine, oxilorphan, nalmexone |

TABLE A-continued

| Class of Agent: | Representative Examples: |
|---|---|
| Sedatives | tracazolate, amobarbital, glutethimide, butalbital |
| Antiepileptic Agents | GABA, γ-vinyl GABA, .γ-acetylenic GABA, apomorphine |
| Stimulants | amphetamine, dextroamphetamine, levamphetamine, aletamine, cypenamine, fencamfamin, fenozolone, zylofuramine, methamphetamine, phenmetrazine, phentermine, amiphenazole, methylphenidate, |
| Anticholinergic Agents | biperiden, cycrimine, procyclidine, trihexyphenidyl |
| Antidepressants | sulpiride, tricyclic antidepressants, E- and Z-isomers of 10-hydroxynortriptyline, 2-hydroxyimipramine, 2-hydroxydesipramine, 8-hydroxychloripramine; hydroxylated metabolites of phenothiazine tranquilizers, 7-hydroxychlorpromazine, desmethyl metabolites of N-methyl benzodiazepine tranquilizers, desmethyldiazepam. |
| Antipsychotic Agents | piperidine-type, fluspirilene, pimozide, penfluridole |
| Medullary Stimulants | ethamivan |
| Barbiturate antagonists | bemegride |
| Sympatomimetic amines and decongestants | ephedrine, pseudoephedrine, oxymetazoline, phenylephrine |
| Cerebral Stimulants | methyprylon, a mild hypnotic; amedalin, bupropion, cartazolate, daledalin, difluanine, fluoxetine, nisoxetine |
| Anaesthetics | thiopental, lidocaine |
| Cardiatonics | digoxin, digitoxin |
| Eichosenoids | prostaglandins, PGEs, $PGE_1$ (alprostadil), $PGI_2$ (prostacyclin or epoprostenol) |
| Hormones | ACTH (corticotropin), LHRH, LH, FSH, HCG, HCS, pituitary and nonpituitary gonadotropins, benzestrol, diethylstilbestrol, somatostatin, neurotensin |
| Enkephalins | $Met^5$-enkephalin, $Leu^5$-enkephalin |
| Anti-Fertility Agents | N,N'-bis(dichloracetyl)-1,8-octamethylenediamine (fertilysin) |
| Endorphins | γ-, α-- and β-endorphins, oxytocin M, vasopressin |
| Anabolic agents | fluoxymesterone, methanstenolone |

Presently preferred pharmaceutical drug compounds according to the methods of the invention are drugs for treating neurologic dysfunction and CNS acting drugs, e.g. dopaminergic agent, androgenic agents, anticonvulsants, anxiolytic agents, antibiotics (i.e., antimicrobial agents), antidepressants, antiviral agents, anticancer or antitumor agents, anti-inflammatory agent, estrogens, progestins. Most preferably, drug compounds for use according to the invention include dopamine, testosterone, phenyloin, GABA, valproic acid, tyrosine, methicillin, oxacillin, benzylpenicilin, cloxacillin, dicloxacillin, desipramine, acyclovir, trifluorothymidine, zidovudine, hydroxy-CCNU, chlorambucil, tryptamine, dexamethasone, hydrocortisone, ethinyl estradiol, norethindrone, estradiol, ethisterone, norgestrel, estrone, estradiol 3-methyl ether, estradiol benzoate, norethynodrel, mestranol, indomethacin, naproxen, FEND, HENU and 5-FU. Examples of preferred pharmaceutical drug compounds for treating neurologic dysfunction are disclosed in TABLE B, below.

TABLE B

CNS-ACTING AGENTS:

Dopamine

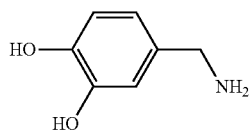

PABA

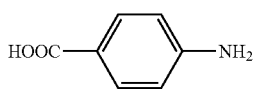

ANTI-VIRAL AGENTS:

Acyclovir

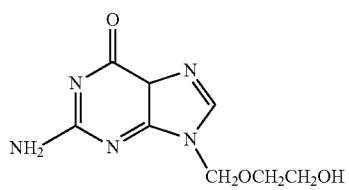

TABLE B-continued
Penciclovir
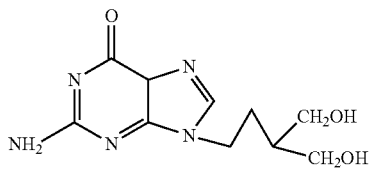
ANTI-MICROBIAL AGENTS:
Trimethoprim
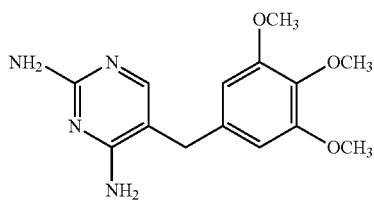 [SMILES: COc1cc(Cc2cnc(N)nc2N)cc(OC)c1OC]
Cephalosporins:
e.g. Cefepime
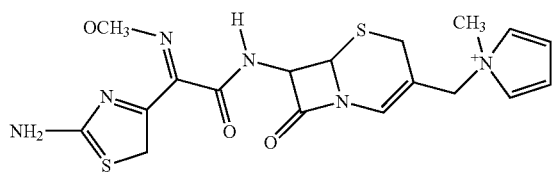
Anti-Fungal Compounds:
e.g. Flucytosine
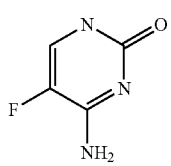
Anti-Parasitic Agents:
e.g. Trimetrexete
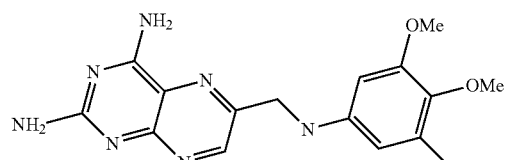
Pentamidine
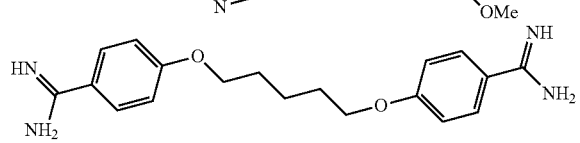
Melarsoprol
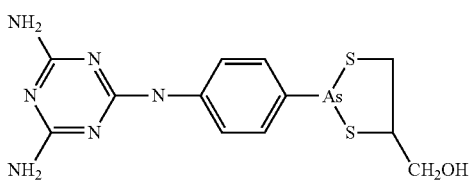
Penicillins:
e.g. Amoxicillin
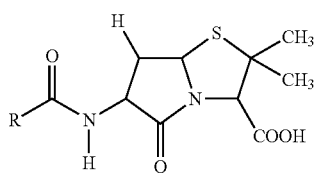
WHERE R = 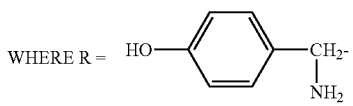

TABLE B-continued
Anti-tuberculosis Agents:
e.g. Ethionamide
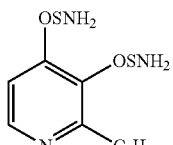
Cycloserine
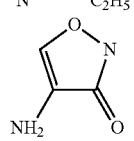
Amino-salicylic acid
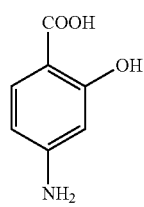
Cycloguanil
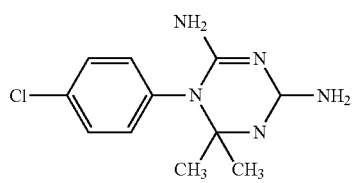 [SMILES: CC1(C)NC(N)N=C(N)N1c1ccc(Cl)cc1]
Pyrimethamine
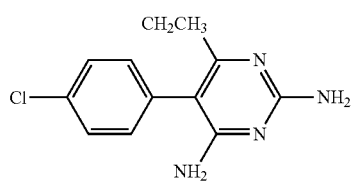 [SMILES: CCc1nc(N)nc(N)c1-c1ccc(Cl)cc1]
CHEMOTHERAPEUTIC AGENTS:
e.g. Methotrexate
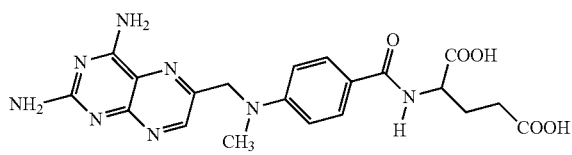
Purines:
e.g. Thioguanine
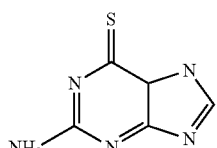
Cisplatin
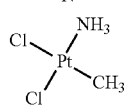
Carboplatin
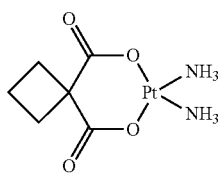

TABLE B-continued
HORMONE-
LIKE AGENTS:
e.g. Thyroxine
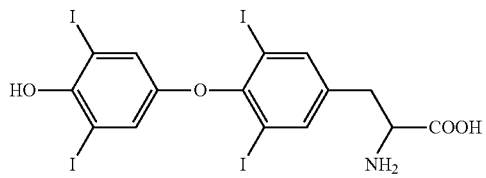 [SMILES: NC(Cc1cc(I)c(Oc2cc(I)c(O)c(I)c2)c(I)c1)C(=O)O]
Pamidronate
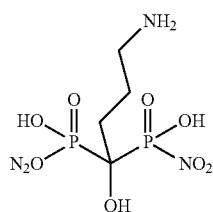
GASTROINTESTINAL-
ACTIVE AGENTS:
e.g. Prokinetic Agents:
Metoclopramide
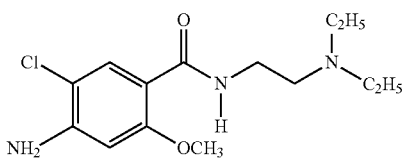 [SMILES: CCN(CC)CCNC(=O)c1cc(Cl)c(N)cc1OC]
ANTI-ARRHYTHMIC
AGENTS:
e.g. Procaineamide
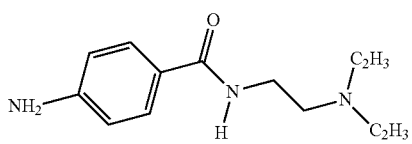
Mexiletine
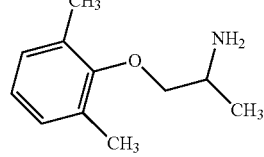
ANTI-HYPERTENSIVE
AGENTS:
e.g. Minoxidil
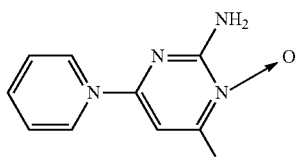
Metyrosine
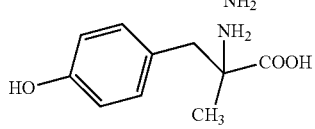
Methyldopa
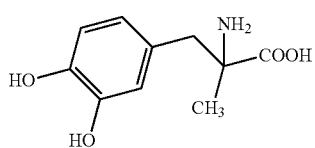

TABLE B-continued

DIURETIC AGENTS:

e.g. Triametene

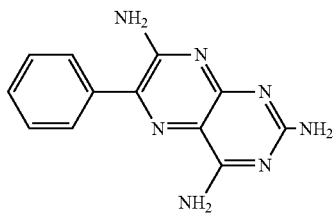 [SMILES: Nc1nc(N)c2nc(-c3ccccc3)c(N)nc2n1]

AUTOCOID AGENTS:

e.g. 2-methyl histamine

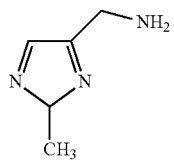

2-pyridyl histamine

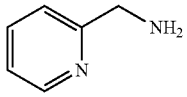

LOCAL ANESTHETICS:

e.g. Benzocaine

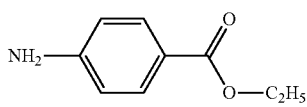

Procaine

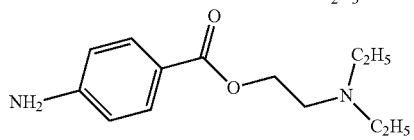

SYMPATHOMIMETICS:

e.g. Phenethylamine

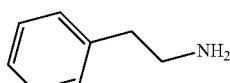

Tyramine

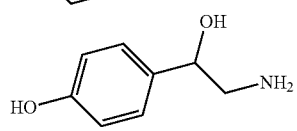

In certain presently preferred embodiments, the N-linked glycosyl prodrug of FORMULA I, further comprises a prodrug compound according to FORMULA IV, below:

namely,

Formula IV

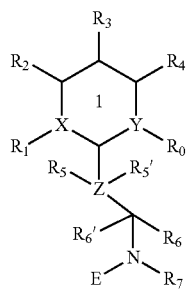

wherein,

Ring 1 comprises am optionally substituted cyclic or heterocyclic ring, or an optionally substituted aromatic ring, composed of about 4 to about 8 carbon atoms, among which are counted "X" and "Y"; preferably, Ring 1 comprises an optionally substituted aryl or heteroaryl ring; and most preferably, a substituted aryl ring; wherein, $R_1$, $R_2$, $R_3$ and $R_4$ comprise the subject optional ring substituents;

each of X and Y are optional and when present comprise a carbon atom, a halogen atom or a lower alkyl, preferably, a carbon atom or a lower alkyl chain having 2 carbon atoms, most preferably a single carbon atom;

$R_0$ comprises hydrogen;

$R_1$, $R_3$ or $R_4$ comprise a group selected from among hydrogen, hydroxyl, halogen, halo-lower alkyl, alkoxy, alkoxy-lower alkyl, halo-alkoxy, thioamido, amidosulfonyl, alkoxy-carbonyl, carboxamide, amino-carbonyl, and alkylamine-carbonyl;

$R_2$ comprises hydroxyl; and, preferably, both $R_2$ and $R_3$ comprise hydroxyl and $R_1$ and $R_4$ comprise hydrogen;

Z is optional and when present comprises a lower alkyl optionally substituted with $R_5$ and $R_{5'}$; preferably, Z is absent or a lower alkyl comprising 1 or 2 carbon atoms; most preferably, Z is absent or a one carbon atom; and, $R_5$ and $R_{5'}$ (when present) and $R_6$ and $R_{6'}$ (when present) are groups selected from among hydrogen, hydroxyl, alkoxyl, carboxyl, alkoxylcarbonyl, aminocarbonyl, alkylamino-carbonyl and dialkylamino-carbonyl;

N comprises a nitrogen atom of a primary or secondary amine or an amide, preferably $R_7$ is a hydrogen or methyl, most preferably, $R_7$ is hydrogen; and, E comprises a saccharide moiety.

The constituents of Formula IV are as set forth (in detail) in Applicant's copending U.S. patent application Ser. No. 09/547,506 (now U.S. Pat. No. 6,548,484 B1), incorporated herein by reference in its entirety.

Representative examples of E-moiety saccharide residues include the following: namely, polyhydroxy $C_1$ aldehydes (e.g. aldoses and ketoaldoses); polyols resulting from e.g., reduction of the $C_1$ aldehyde carbonyl to a hydroxyl (e.g., alditols and ketoses); polyhdyroxy acids resulting e.g., from oxidation of the $C_1$ aldehyde and/or the chain terminal hydroxyl (e.g., aldonic, ketoaldonic, aldaric and ketoaldaric); amino-sugars resulting from replacement of any hydroxyl in the chain with an amino (e.g., aldosamines and ketosamines); aldehydro-acids resulting e.g. from oxidation of only the chain terminal hydroxyl in an aldehydro-sugar (e.g., uronic acids and keto-uronic acids); and their various lactones, i.e., cyclic esters of hydroxy carboxylic acids containing one 1-oxacycloalkan-2-one structure. The subject sugars may be straight chains and/or cyclic 0.3-, 4-, 5-, 6-, 7-, 8- and 9-membered sugar residues (e.g., hemiacetals and acetals) optionally substituted and linked with the D-moiety as set forth, supra. Representative triosyl residues include the aldoses D- and L-glyceraldehyde and derivatives thereof e.g., glyceraldehyde and glyceric acid phosphates; the keto-sugars D- and L-dihydroxyacetone and derivatives thereof. Representative tetraosyl residues include the aldoses D- and L-erythrose, threose, streptose and apiose; the keto-sugars D- and L-erythrulose; and derivatives thereof. Representative pentosyl residues include the D- and L-aldoses ribose, arabinose, xylose and lyxose; the D- and L-ketoses ribulose and xylulose; and, derivatives thereof. Representative hexosyl residues include aldosyl, furanosyl and pyranosyl sugars, e.g., cyclic and acyclic D- and L-aldoses such as allose, altrose, glucose, mannose, gulose, idose, galactose, talose, fructose, glucono-1,4-lactone, glucaro-1,4:6,3-dilactone, gluconofuranono-6,3-lactone; the ketoses ribo-hexylose, arabino-hexylolose, xylo-hexylose and lyxo-hexylose; and derivatives thereof. Representative 7-membered residues (i.e., heptosyl residues) include e.g., sedoheptulose and derivatives thereof; and, representative 9-membered residues (i.e., nonosyl residues) include N-acetylneuraminic acid and derivatives thereof. Also representative are, 2-deoxy-ribose, 6-deoxyglucose and 2-deoxyglucose, xyloascorbyllactone, digitoxose (2-deoxyaltromethylose), fucose (6-deoxy-galactose), gluconolactone, galaconolactone, rhamnose (6-deoxy-mannose), fructose (2-keto-arabohexose), aldaric acids, alditols, aldonic acids, ketoaldonic acids, and amino sugars; with the proviso that the E-moiety is not a cyclodextrin. Representative alditols include e.g., erythritol, threitol, ribitol, arabinitol, xylitol, lyxitol, glucitol, allositol, altrositol, mannositol, gulositol, idositol, galactositol, talositol and their derivatives. Representative aldonic acids include erythronic acid, threonic acid, ribonic acid, arabinonic acid, xylonic acid, lyxonic acid, gluconic acid, allonic acid, altronic acid, mannonic acid, gulonic acid, idonic acid, galactonic acid, tolonic acid and their derivatives. Representative ketoaldonic acids include erythro-tetraulosonic acid, threo-tetraulosonic acid, ribo-pentulosonic acid, arabino-pentulosonic acid, xylo-pentulosonic acid, lyxo-pentulosonic acid, gluco-hexylosonic acid, allo-hexylosonic acid, altro-hexylosonic acid, manno-hexylosonic acid, gulo-hexylosonic acid, ido-hexylosonic acid, galacto-hexylosonic acid, talo-hexylosonic acid and their derivatives. Representative aldaric acids include erythraric acid, threaric acid, ribaric acid, arabinaric acid, xylaric acid, lyxaric acid, aldaric acid, altraric acid, glucaric acid, mannaric acid, gularic acid, idaric acid, galactaric acid, talaric acid and their derivatives. Representative of amino sugar include erhtyrosamine, threosamine, ribosamine, arabinosamine, xylosamine, lyxosamine, allosamine, altrosamine, glucosamine, N-acetylglucosamine, N-methlglucosamine mannosamine, gulosamine, idosamine, galactosamine, talosamine and their derivatives. Representative uronic acids include erythrosuronic acid, threosuronic acid, ribosuronic acid, arabinosuronic acid, xylosuronic acid, lyxosuronic acid, allosuronic acid, altrosuronic acid, glucuronic acid, mannosuronic acid, gulosuronic acid, idosuronic acid, galactosuronic acid, talosuronic acid and their derivatives. Representative keto-uronic acids include keto-erythrosuronic acid, keto-threosuronic acid, keto-ribosuronic acid, keto-arabinosuronic acid, keto-xylosuronic acid, keto-lyxosuronic acid, keto-allosuronic acid, keto-altrosuronic acid, keto-glucuronic acid, keto-mannosuronic acid, keto-gulosuronic acid, keto-idosuronic acid, keto-galactosuronic acid, keto-talosuronic acid and their derivatives. Representative lactones include erythrolactone, threolactone, ribolactone, arabinolactone, xyloslactone, lyxoslactone, allolactone, altrolacone, glucolactone, mannolactone, gulolactone, idolactone, galactolactone, talolactone and their derivatives.

Preferably, the subject E-moiety comprises an aldose or ketose pentose or hexose sugar selected from the group consisting of D- and L-enantiomers of ribose, glucose, galactose, mannose, arabinose, allose, altrose, gulose, idose, talose and their substituted derivatives. Most preferably, the subject E-moiety comprises an aldose pentosyl or hexosyl sugar selected from ribose, glucose, galactose, glucosamine, galactosamine, N-acetylglucosamine, N-acetylgalactosamine, N-acetyl ribosamine, xylose, mannose and arabinose.

"Halogen" is intended to mean a fluorine, chlorine, bromine, or sulfur atom or ion or group. Preferred halo groups are chlorine, bromine, thiol and sulfonyl and most preferred, chlorine.

"Lower alkyl" is intended to mean a hydrocarbon chain containing fewer than six carbon atoms, preferably fewer than four and most preferably two or 3 carbon atoms. Representative lower alkyl groups include methyl, ethyl, n-propyl, i-propyl, n-butyl, t-butyl and i-butyl. Presently preferred alkyls are methyl, ethyl or i-propyl, and most preferably, ethyl.

"Substituted lower alkyl" is intended to mean a lower alkyl in which one or more of the hydrogen atoms are replaced by a substituent group. Representative substituent groups include hydroxy, alkoxy, halogen, amino, amido, carboxyl, thiol, sulfonyl, methoxy and the like.

"Halo-lower alkyl" is intended to mean a lower alkyl in which one or more of the hydrogen atoms on the hydrocarbon chain has been replaced by a halogen atom.

"Cycloalkyl" is intended to mean a closed saturated monocyclic hydrocarbon ring made up of about 4 to about 9 carbon atoms, preferably about 5 to about 7 carbon atoms and most preferably 6 carbon atoms. Representative examples of cycloalkyl compounds include phenyl, piperidyl, piperazinyl, diazinyl, morpholinyl, isooxazoanyl and the like.

"Heterocyclic" is intended to mean a close saturated monocyclic ring made up of about 4 to about 8 carbon atoms and about 1 to about 2 non-carbon atoms; preferably, about 5 to about 6 carbon atoms and 1 non-carbon halogen or oxygen atom; and, most preferably 5 carbon atoms and 1 non-carbon halogen or oxygen atom.

"Aromatic", and "aryl", are used interchangeably to mean a closed unsaturated monocyclic hydrocarbon ring system made up of about 3 to about 9 carbon atoms having a delocalized π-electron system. Preferably, the subject aryl ring is made up of about 5 to about 7 carbon atoms and most preferably, 6 carbon atoms. Representative aromatic rings include benzyl, pyranyl, pyridyl, pyrimidinyl, thiadiazinyl and pyridazinyl, with benzyl preferred.

"Amine" is intended to mean an —NHR substituent group.

"Amide" is intended to mean an —C(O)N—(R')R" or —HNC(O) substituent group, where R' and R" are hydrogen or a substituent such as hydroxy, lower alkyl, amino, or the like. Preferred amino groups are those wherein R' or R" is hydrogen.

"Alkoxy" is intended to mean an —OR substituent group.

"Halo-lower alkyl" is intended to mean a halogen substituted lower alkyl; preferably, a halogen substituted lower alkyl having 2 to 6 carbon atoms; most, preferably, a chlorine or fluorine substituted lower alkyl having 2 to 4 carbon atoms.

"Alkoxy-lower alkyl" is intended to mean an alkoxy compound, supra, wherein R comprises a lower alkyl; preferably a 2 to 6 carbon lower alkyl; and most preferably, a 2 to 4 carbon lower alkyl.

"Thioalkoxy" is intended to mean an —SOR substituent group.

"Aminocarbonyl" is intended to mean a —C(O)NH$_2$ substituent group.

"Alkylaminocarbonyl" is intended to mean a —C(O)NHR substituent group wherein R is a lower alkyl.

"Alkoxycarbonyl" is intended to mean a —C(O)OR substituent group.

"Carboxamide" is intended to mean a —NR'COR substituent group.

"Dialkylaminocarbonyl" is intended to mean a —C(O)NR'R substituent group, wherein R' and R constitute lower alkyl groups.

"Haloalkoxy" is intended to mean a —OR substituent group where R is a haloalkyl.

"Oxyamido" is intended to mean a —OC(O)NH— or —HNC(O)O-substituent.

"Thioamido" is intended to mean a —SC(O)NH— or —HNC(S)— substituent.

"Amidosulfonyl" is intended to mean a —NHSO$_2$— substituent.

In other embodiments, the invention provides methods of using pharmaceutical compositions containing one or more compounds according to FORMULA I, supra, in combination with optional stabilizers, carriers, binders, buffers, excipients, emollients, disintegrants, lubricating agents, antimicrobial agents and the like. For oral administration, the instant methods may employ pharmaceutical compositions that are liquid, solid or encapsulated. For perenteral administration, the instant methods may employ pharmaceutical compositions that are sterile liquids or solids, e.g., as provided in a powdered or granulated form suitable for reconstitution.

The instant methods may employ compounds to be administered alone or in combination with pharmaceutically acceptable carriers, e.g. in either single or multiple doses. Suitable pharmaceutical carriers may include inert solid diluents or fillers, sterile aqueous solutions, and various nontoxic organic solvents. The pharmaceutical compositions formed by combining a compound according to FORMULA I with a pharmaceutically acceptable carrier may be administered according to the instant methods in a variety of dosage forms such as tablets, lozenges, syrups, injectable solutions, and the like. The subject pharmaceutical carriers can, if desired, contain additional ingredients such as flavorings, binders, excipients, and the like. Thus, for purposes of the instant oral administration, tablets containing various excipients such as sodium citrate, calcium carbonate, and calcium phosphate may be employed along with various disintegrants such as starch, and preferably potato or tapioca starch, alginic acid, and certain complex silicates, together with binding agents such as polyvinylpyrolidone, sucrose, gelatin, and acacia. Additionally, lubricating agents, such as magnesium stearate, sodium lauryl sulfate, and talc may be useful for tableting purposes. Solid compositions of a similar type may also be employed as fillers in salt and hard-filled gelatin capsules. Preferred materials for this purpose include lactose or milk sugar and high molecular weight polyethylene glycols. When aqueous suspensions of elixirs are desired for oral administration according to the instant methods, the compound therein may be combined with various sweetening or flavoring agents, colored matter or dyes, and if desired, emulsifying or suspending agents, together with diluents such as water, ethanol, propylene glycol, glycerin, and combinations thereof. For parenteral administration according to the instant methods, solutions may be prepared in sesame or peanut oil or in aqueous polypropylene glycol, as well as sterile aqueous saline solutions of a corresponding water-soluble pharmaceutically acceptable metal salt, e.g. as disclosed supra. The subject aqueous solution is preferably suitably buffered if necessary and the liquid diluent first rendered isotonic with sufficient saline or glucose. Such aqueous solutions of compounds according to FORMULA I may be particularly suitable for intravenous, intramuscular, subcutaneous, and intraperitoneal injection. The subject sterile aqueous media employed are obtainable by standard techniques well known to those skilled in the art.

For use in one or more of the instant methods, it may prove desirable to stabilize a compound according to FORMULA I, e.g. to increase shelf life and/or pharmacokinetic half-life. Shelf-life stability may be improved by adding excipients such as: a) hydrophobic agents (e.g., glycerol); b) non-linked sugars (e.g., sucrose, mannose, sorbitol, rhamnose, xylose); c) non-linked complex carbohydrates (e.g., lactose); and/or d) bacteriostatic agents. For use in the instant methods, pharmacokinetic half-lives may vary depending upon the saccharide moiety selected, e.g., whether a sugar or a digestible oligosaccharide, or the nature of the sugar R-group constituents. For use in the instant methods, pharmacokinetic half-life and pharmacodynamics may also be modified e.g. by: a) encapsulation; b) controlling the degree of hydration; and, c) controlling the electrostatic charge and hydrophobicity of the sugar constituents.

For use according to the instant methods, pharmaceutically acceptable salts can be prepared from the instant compounds by conventional methods. Thus, such salts may, for example, be prepared by treating a compound according to FORMULA I with an aqueous solution of the desired pharmaceutically acceptable metallic hydroxide or other metallic base and evaporating the resulting solution to dryness, preferably under reduced pressure in a nitrogen atmosphere. Alternatively, a solution of the subject compound may be mixed with an alkoxide to the desired metal, and the solution subsequently evaporated to dryness. The pharmaceutically acceptable hydroxides, bases, and alkoxides include those with cations for this purpose, including (but not limited to), potassium, sodium, ammonium, calcium, and magnesium. Other representative pharmaceutically acceptable salts include hydrochloride, hydrobromide, sulfate, bisulfate, acetate, oxalate, valarate, oleate, laurate, borate, benzoate, lactate, phosphate, tosulate, citrate, maleate, furmarate, succinate, tartrate, and the like.

For use in the instant methods, freely-soluble salts of a compound according to FORMULA I may be converted to a salt of a lower solubility in a body fluid, e.g. by modification with a slightly water-soluble pharmaceutically acceptable salt such as tannic or palmoic acid, or by inclusion in a time-release formulation such as covalently coupled to a larger carrier, or in timed-release capsules and the like. In general, the acid addition salts of the subject compounds with pharmaceutically acceptable acids will be biologically equivalent to the compounds themselves. Pharmaceutically acceptable salts can be prepared from the compounds by conventional methods. Thus, such salts are, for example, prepared by treating with an aqueous solution of the desired pharmaceutically acceptable metallic hydroxide or other metallic base and evaporating the resulting solution to dryness, preferably under reduced pressure in a nitrogen atmosphere. Alternatively, a solution of a compound is mixed with an alkoxide to the desired metal, and the solution subsequently evaporated to dryness. The pharmaceutically acceptable hydroxides, bases, and alkoxides include those with cations for this purpose, including (but not limited to), potassium, sodium, ammonium, calcium, and magnesium. Other representative pharmaceutically acceptable salts include hydrochloride, hydrobromide, sulfate, bisulfate, acetate, oxalate, valarate, oleate, laurate, borate, benzoate, lactate, phosphate, tosylate, citrate, maleate, furmarate, succinate, tartrate, and the like.

The preferred pharmaceutical compositions for inocula and dosage for use in the instant methods will vary with the clinical indication. The inocula may typically be prepared from a dried compound by suspending the compound in a physiologically acceptable diluent such as water, saline, or phosphate-buffered saline. Some variation in dosage will necessarily occur depending upon the condition of the patient being treated, and the physician will, in any event, determine the appropriate dose for the individual patient. The effective amount of the instant compound per unit dose depends, among other things, on the body weight, physiology, and chosen inoculation regimen. A unit dose of a compound according to FORMULA I refers to the weight of the subject compound without the weight of carrier (when carrier is used). Generally, the amount of active ingredient administered to a subject in need thereof according to the practice of the invention will be in the range of about 1 mg/day to about 2.5 gm/day. Single unit dosage forms and multi-use dosage forms are considered within the scope of the invention, as disclosed further below.

Pharmaceutically acceptable carriers may be formed, filled and sealed for ease of use according to the methods of the invention. Representative forming, filling and sealing methods are known in the pharmaceutical arts. For instant, the subject compositions may be formulated with pharmaceutically acceptable carriers into pharmaceutical preparations suitable for inclusion in timed-release capsules, tablets, lozenges, syrups and the like.

For treatments of local peripheral neurologic dysfunctions, the subject compounds may be provided in an emollient cream. Representative examples of emollient pharmaceutically acceptable carriers include oil-in-water and water-in-oil emulsions, i.e., as are known to those skilled in the pharmaceutical arts.

Pharmaceutically acceptable salts may be prepared from the subject compounds by conventional methods. For example, such salts may be prepared by treating one or more of the subject compounds with an aqueous solution of the desired pharmaceutically acceptable metallic hydroxide or other metallic base and evaporating the resulting solution to dryness, preferably under reduced pressure in a nitrogen atmosphere. Alternatively, a solution of the subject compound may be mixed with an alkoxide to the desired metal, and the solution subsequently evaporated to dryness. The pharmaceutically acceptable hydroxides, bases, and alkoxides include those with cations for this purpose, including (but not limited to), potassium, sodium, ammonium, calcium, and magnesium. Other representative pharmaceutically acceptable salts include hydrochloride, hydrobromide, sulfate, bisulfate, acetate, oxalate, valarate, oleate, laurate, borate, benzoate, lactate, phosphate, tosulate, citrate, maleate, furmarate, succinate, tartrate, and the like.

In alternative embodiments, the invention provides different routes for delivery of compounds according to FORMULA I as may be suitable for use in the different disease states and sites where treatment is required. For topical, intrathecal, intramuscular or intra-rectal application it may prove desirable to apply the subject compounds as a salve, ointment or emollient pharmaceutical composition at the local site, or to place an impregnated bandage or a dermal timed-release lipid-soluble patch. For intra-rectal application it may prove desirable to apply the subject compounds e.g. in a suppository. In other embodiments, it may prove desirable to administer the subject compositions by intranasal or intrabronchial instillation (e.g., as pharmaceutical compositions suitable for use in a nebulizer), or by gastrointestinal delivery (e.g., with a capsule, tablet, trouch or suppository). Also contemplated are suppositories for urethral and vaginal use. In one preferred embodiment, the subject pharmaceutical compositions are administered via suppository taking advantage of saccharide transporters in the rectum for transport into the blood stream in a timed-release type manner e.g. providing possible metabolic replacement therapy in a patient with a Parkinson's or related disease.

Embodiments of the invention provide treatments for diseases including e.g., central and peripheral nervous system dysfunctions, neuromotor dysfunction, hypertension, hypotension and cardiovascular diseases. In other embodiments, treatments may be administered purposefully to agonize, partially agonize or antagonize a dopamine receptor in a peripheral tissue containing nervous enervation, e.g., in an organ or a vascularized endocrine tissue. For example, embodiments of the invention may provide treatments ameliorating certain symptoms of Parkinson's, tardive dyskinesia, hypertension, congestive heart disease, hyperprolactinemia, epilepsy, Alzheimer's disease and the like.

In yet other embodiments, the invention provides therapeutic methods in which a relatively high concentration of active ingredients (e.g., up to 500 mg/ml) is included in a relatively small volume (e.g., up to about 500 mg/ml) taking advantage of the special aqueous solubility of the prodrug compounds according to FORMULA I. In certain embodiments, the invention provides improved treatment methods using relatively high concentrations of the subject drugs in multi-dose, time-release, subcutaneous and intradermal, buccal, trouch, and suppository preparations. In other embodiments, the instant treatment methods may also be especially useful for achieving steady state plasma levels in subjects in need thereof. Where conventional methods of administration may be ineffective in certain patients, the instant methods, i.e., employing high solubility compounds according to FORMULA I, make it feasible to administer metabolic replacement therapy in a multi-dosage form, e.g. via an implantable mini-pump (such as used for delivery of insulin in patients with Type 1 insulin-dependent diabetes mellitus).

Embodiments of the invention provide methods for improving the aqueous solubility of poorly soluble pharmaceutical agents and resultant compositions with improved aqueous solubility. The instant compositions have improved bioavailability providing a pharmacologically effective therapeutic unit dosage at a lower level of administered drug compound. The instant methods thus provide novel formulations and resultant pharmaceutical compositions wherein lower concentrations of pharmaceutical agents provides cost-savings, and at the same time, improvements in efficacy. Bioavailability, in this context, is intended to mean improved pharmacokinetic rates of delivery occassioned e.g., by more effective transport from the gastrointestinal system into blood, or by greater solubility in bodily fluids, as well as, improved stability of drug levels in bodily fluids. In addition to delivery rate improvements, the instant methods provide novel pharmaceutical compositions not previously possible with poorly soluble pharmaceutical agents. In a first representative example, new activities and new uses may be provided for antidiarrheal agents because of improved aqueous solubility, e.g. uses of Imodium® (loperamide) in controlling systemic electrolyte balance and/or vascular smooth muscle tone. In a second representative example, novel pharmaceutical compositions are provided, e.g., petroleum based delivery formulations for Acyclovir®. In a third representative example, novel therapeutic methods are provided, e.g., uses of Acyclovir® in petroleum based formulations for prophylactic topical treatments of oral and genital Herpes infections.

Embodiments of the invention provide treatments for neurologic dysfunctions. According to the instant methods, a purpose of therapy in an acute setting may be to rapidly increase the concentration of one or more of the instant composition in a tissue, e.g., by a bolus intravenous injection. Alternatively, in other cases it may desirable to deliver the composition over a longer period of time, e.g., by infusion. The route of delivery according to the instant methods is determined by the disease and the site where treatment is required. For topical application, it may prove desirable to apply the compositions at the local site (e.g., by placing a needle into the tissue at that site) or by placing a timed-release dermal patch); while in a more acute disease clinical setting it may prove desirable to administer the compositions systemically. For other indications the instant compounds may be delivered by intravenous, intraperitoneal, intramuscular, subcutaneous and intradermal injection, as well as, by intranasal and intrabronchial instillation (e.g., with a nebulizer), transdermal delivery (e.g., with a lipid-soluble carrier in a skin patch), or gastrointestinal delivery (e.g., with a capsule or tablet). The preferred therapeutic compositions for inocula and dosage will vary with the clinical indication. The inocula may typically prepared from a dried compound, e.g. by suspending the compound in a physiologically acceptable diluent such as water, saline, or phosphate-buffered saline. Some variation in dosage will necessarily occur depending upon the condition of the patient being treated, and the physician will, in any event, determine the appropriate dose for the individual patient. Since the pharmacokinetics and pharmacodynamics of the instant compounds will vary somewhat in different patients, the most preferred method for achieving a therapeutic concentration in a tissue is to gradually escalate the dosage and monitor the clinical effects. The initial dose, for such an escalating dosage regimen of therapy, will depend upon the route of administration.

In other embodiments, the invention provides methods prophylactic and therapeutic uses in treatment of neuropathophysiologic conditions in man and domestic animals, i.e. involving the step of administering to a subject in need thereof a compound according to FORMULA I, supra. In certain alternative embodiments, the method may involve administration of an intravenous bolus injection or perfusion, or may involve administration during (or after) surgery, or a prophylactic administration. In certain other embodiments, the instant administration may involve a combination therapy, e.g., a compound according to FORMULA I and a second drug, e.g., an anti-coagulant, anti-infective or anti-hypertensive agent.

The route of delivery of the subject preparations, according to the instant methods, determined by the particular disease. For topical application it may be useful to apply the instant compounds at the local site (e.g., by injection, while for other indications the preparations may be delivered by intravenous, intraperitoneal, intramuscular, subcutaneous, intranasal, and intradermal injection, as well as, by transdermal delivery (e.g., with a lipid-soluble carrier in a skin patch placed on the skin), or even by oral and/or gastrointestinal delivery (e.g., with a capsule, tablet or suppository).

In certain preferred embodiments, the invention provides methods for administering to a subject in need thereof one or more dopaminergic agents according to FORMULA I in combination with an agent capable of stimulating intestinal or neural glucose transporter activity, e.g., IGF-1, glucagon, vascular infusions of glucose and the like. The instant combination treatments may be effected by the same route, (e.g., both administered orally), or alternatively, by different routes. Instruction is provided that intestinal glucose saccharide co-transporters exhibit circadian periodicity and expression is inducible by dietary carbohydrate (e.g., see Rhoads et al., 1998), and negatively regulated by leptin (e.g., see Lostao et al. 1998). Thus, in certain embodiments, treatment regimens for oral administration may include instructions to take one or more of the subject compounds orally with a feeding that includes dietary carbohydrate, and preferably, in the morning within about 5 to about 20 minutes after the first meal, and in the evening before, during or within about 5 to about 20 minutes after an evening meal. Instruction is also provided that during the instant treatment the following are to be avoided because they may alter saccharide transporter activity: namely, (i) high cholesterol diet; (ii) co-administration with oral calcium channel blockers (e.g., see Hyson et al. 1996, 1997); (iii) erythromycin (Navarro et al., 1993); and, (iv) barbiturates (Haspel et al., 1999).

Methods for determining that a test compound according to FORMULA I, i.e., with a drug selected from TABLE A or TABLE B, is suitable for use in one or more of the instant methods, (i.e., for treating neurologic dysfunction or for use as a CNS-acting drug), are known to those skilled in the art of neuropsychopharmacology. For instance, the test compound may be evaluated in behavioral tests in experimental animals; e.g., to determine whether it exhibits Pergolide-like dopaminergic activity. For example, oral dosing of mice with test compound at doses of about 0.3-300 mg/kg; monitoring for lowering of body temperature induced by reserpine, or monitoring for increased hexobarbital-induced sleep time, or for slowed respiration, or hyporeactiveness, ptosis or placing loss. Pergolide, used as a positive control, should reverse reserpine-induced hypothermia with no effect on reflex reactions, i.e., as evaluated by electroshock-, pentylenetretrazol (pentetrazol)- or strychnine-induced seizures. Preferably, the subject compounds when administered according to the methods of the invention are without effect on reflex reactions. Test dopaminergic compounds according to FORMULA I, (and Pergolide control), should not effect oxotremorine-induced tremors or salivation, grip strength or tail-flick reactions; and, should not alter shuttle-avoidance behavior in rats at an oral dosage of about 0.1-30 mg/kg.

Stimulation induced release: Dopamine-like agonist CNS-acting drug activity of a test compound may be studied in vitro by loading rat spleen strips with a $^3$H-radiolabeled test compound according to FORMULA I, then exposing the strips to supramaximal electrical field stimulation, and monitoring release, e.g., using methods such as those disclosed by Benesics et al. (1997).

Locomotor activity in murine test models: Sedatives and tranquilizers decrease general locomotor activity while stimulants increase general locomotor activity. The CNS-acting effects of a test compound may be evaluated in an experimental animal model using various routes of administration, e.g., intraperitoneal, subcutaneous, intramuscular, intradermal and/or intravenous injections. Effects of test compounds and preparations on the general motor activity of mice may be determined, e.g., during a 60-min period using a Stoelting electronic activity monitor. Dose-response curves may be obtained from which a half-maximally effective value may be calculated. Additional models of assessing possible CNS-acting drug effects of a test compound include, e.g. MPTP-lesioned primates and rats and vacuous chewing and grooming behaviors in 6-hydroxydopamine lesioned rats.

Anticonvulsant Activity in Mice: Anticonvulsant activity of a putative CNS-acting test compound may be measured e.g. in an experimental animal model where prophylactic prevention (e.g., administered 24 hrs. before induction of convulsions) or therapeutic delay in the onset of (e.g. bicuculline-induced epileptic seizures) is evaluated, e.g. in mice.

Analgesic Activity Tests: That a test compound is a CNS-acting drug with analgesic activity similar to a dopaminergic agonists may be assessed using an experimental animal model known to those of skill in the art to be useful for assessing analgesia, e.g., formalin-, hotplate- or carbon-tetrachloride-induced analgesic models. Analgesic activity in a formalin model may e.g., be determined according to methods such as those disclosed by Morgan et al., 1991.

Memory Tests: That a test compound is a CNS-acting drug having an effect on memory potentiation or impairment may be evaluated, e.g., in an experimental animal model involving pre-treatment with the test compound and use of a one trial inhibitory avoidance test, e.g. in mice with and without foot shock to test for memory consolidation in the presence and absence of the treatments with the test compound.

Dopamine Transporter (DAT1): That a test compound according to the invention is transportable by DAT may be determined using methods known to those of ordinary skill in the art. The mouse, rat and human DAT1 genes are cloned (Wu et al., 1999; Shimada et al., 1991; Kilty et al., 1991; Giros et al., 1991; Vandenbergh, et al., 1992), sequences are reported (e.g., see U.S. Pat. No. 5,756,307) and homozygous and knock-out mice (e.g., see Jaber et al., 1999; reviewed in Gainetdinov et al., 1999) and cell lines (e.g. 1RB3AN27 dopamine neurons, see Clarkson et al., 1999; HEK 293 stably transfected cells, see Storch et al.; PC12 stably transfected cells, see Melikian et al., 1999; in MDCK stably transfected cells, see Wu et al., 1999) have been prepared. Other in vitro assays for assessing DAT transportability of a test compound include ligand-binding studies conducted e.g., with rat brain slices or rat caudate putamen membrane preparations.

MPTP-Treated Mice: Progressive decreased expression of dopamine receptors and dopamine transporters accompanies treatments of mice with MPTP (1-methyl-4-phenyl-1,2,3,6-tetrahydropyridine; e.g. see Kilbourn et al., 2000), i.e., a similar pattern of changes to those observed in early onset Parkinson's disease by imaging (e.g., see Verhoeff, 1999). While certain of the neurophysiologic attributes of MPTP-treated mice may not mirror Parkinsonism, this animal model is widely used to evaluate the potential effects of test compounds in treatments for Parkinson's disease.

Additional disclosure of the N-linked glycosyl prodrug pharmaceutical compositions is contained within Applicant's copending U.S. patent application Ser. No. 09/547,506 (now U.S. Pat. No. 6,548,484 B1), incorporated herein by reference in its entirety.

EXAMPLE 1

Preparation of Dopamine Gluconamide and Dopamine Gluconamine

Representative compounds for use according to the instant methods were synthesized as disclosed in co-pending U.S. patent application Ser. No. 09/547,506 (now U.S. Pat. No. 6,548,484 B1), incorporated herein by reference in its entirety. Briefly, gluconolactone and 3-hydroxytyramine were reacted slowly in methanol to form a white solid dopamine gluconamide precipitant. The product was collected by filtration, washing and drying in vacuo (i.e., dopamine gluconamide, Compound #1, below).

EXAMPLE 1-1

Preparation of Dopamine Gluconamide

Scheme 1

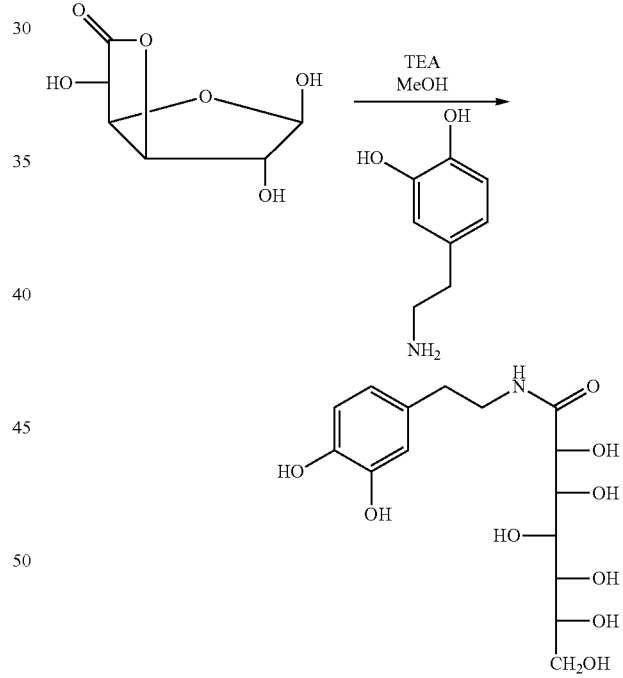

Gluconolactone (1.9 gm, 10.5 mmol) and triethylamine (TEA; 1.1 gm, 10.5 mmol) were added to methanol (25 mL) in a 100 mL round bottom flask with stirring. The gluconolactone was allowed to dissolve. When the solid was dissolved, the solution was stirred for an additional 10 minutes and then 3-hydroxytyramine (2.0 gm, 10.5 mmol) was added slowly, i.e., allowing it to dissolve. The reaction mixture was stirred in the dark for about 2 hrs. during which time a white solid precipitant appeared. The white solid precipitant was collected by filtration, washed with methanol (5 mL) and dried in vacuo for 6 hrs. to give dopamine gluconamide (1.69 gm, 5.10 mmol, 48.6% yield). Melting point of the synthesis product was 154-155° C. Predicted: $C_{14}H_{21}N_1$ (331.32): C—

50.75%, H—6.39%, N—4.23%; analysis results of synthetic product: C, 50.65; H, 6.63; N, 4.444.

EXAMPLE 1-2

Protection of Aromatic Dopamine Hydroxyl Residues

Scheme 2

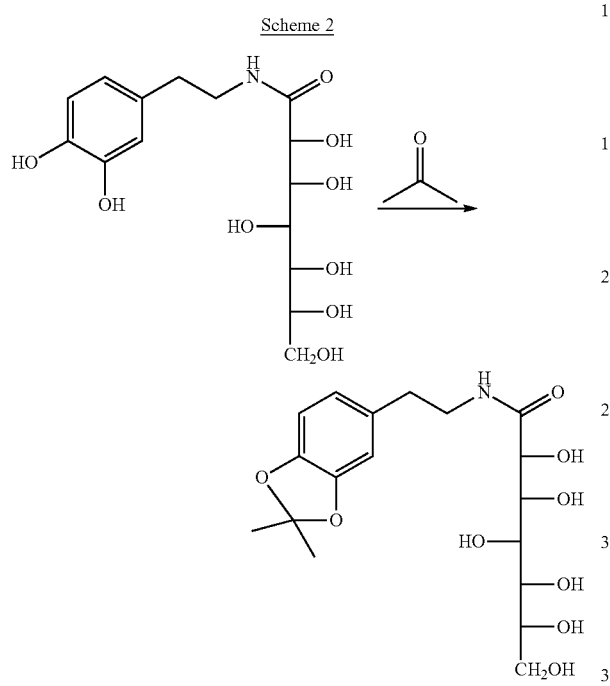

Dopamine gluconamide (EXAMPLE 1, supra; 0.75 gm, 2.26 mmol) was added to acetone (40 mL) in a 100 mL round bottom flask with stirring. Then, the reaction mixture was refluxed for 2 hrs., after which time it was allowed to cool to room temperature (about 22-25° C.). The resultant white solid was removed by filtration and dried in vacuo for 7 hrs. yielding the isopropylidine protected dopamine gluconamide (0.68 gm, 1.83 mmol, 81.0% yield). Melting point of the synthesis product was 170° C.

EXAMPLE 1-3

Reduction of Isoproylidene Protected Dopamine Gluconamide

Scheme 3

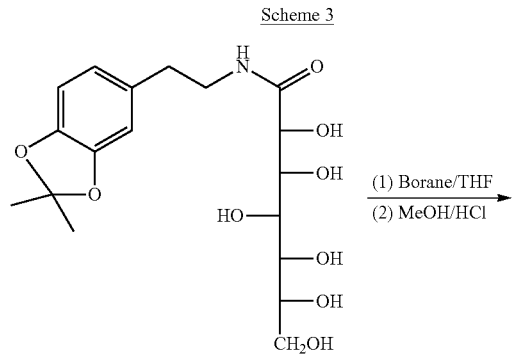

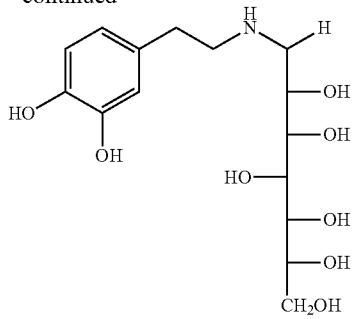

Isopropylidene protected dopamine gluconamide (EXAMPLE 2, supra; 0.68 gm, 1.83 mmol) was slowly added to a 1 M Borane solution in THF (25 ml) in a 100 mL round bottom flask, with stirring. The reaction mixture was refluxed for 2 hrs. and then allowed to cool to room temperature. Excess solvent was removed by rotary evaporation. Methanolic HCl was added to the resultant residue and the solution refluxed for 2 hrs., after which time solvent was removed by evaporation and the solid recrystallized using a mixture of acetonitrile and ethanol. The recrystallized reduced dopamine gluconamide product was dried in vacuo for 6 hrs. giving the dopamine gluconamine-HCl salt (0.22 gm, 0.62 mmol, 33.8% recovery). Melting point for the synthesis product was 151-152° C. Predicted $C_{14}H_{24}N_1$ (353.80); C, 47.53, H, 6.84; N, 3.96; Analysis result of synthesis product: C, 47.48; H, 6.93; N, 3.88.

EXAMPLE 1-4

Preparation of Dopamine Ribonamide

D-(+)-Ribonic acid gamma-lactone (2.0 gm, 13.5 mmol) was added to methanol (25 mL) in a 100 mL round bottom flask with stirring until dissolved, and then an additional 5 min. 3-Hydroxytyramine (2.6 gm, 13.5 mmol) was added slowly, allowing it to dissolve, with stirring, over the course of about 10 minutes. Triethylamine (1.4 gm, 13.5 mmol) was then added and the reaction mixture refluxed for 4 hr. in the dark, during which time the solution acquired a slight yellow color. Solvents were removed by rotary evaporation using anhydrous ethanol as an azeotrope to remove any residual water. The resultant dried product constituted a thick syrup which solidified upon standing (1 hr.) to give a white solid. The white solid product was stirred (1 hr.) with acetone (40 mL), again resulting in a white solid as a product. The resultant solid was collected by filtration and dried in vacuo for 6 hrs. yielding dopamine ribonamide (3.83 gm, 12.7 mmol, 94.1% yield.) $^1H$ and $^{13}C$-NMR results and CHN analyses were consistent with structure. Melting point was 90-91° C. Predicted $C_{13}H_{19}N_1$: (301.30): C, 51.82; H, 6.36; N, 4.65; Analysis results of synthesis product: C, 51.67; H, 6.40; N, 4.69.

EXAMPLE 1-5

Preparation of Dopamine Isopropylidine Ribonamide

Aromatic hydroxyl groups in dopamine ribonamide were protected by synthesizing the isopropylidine compound. Dopamine ribonamide (EXAMPLE 4; 1.0 gm, 3.32 mmol) was added to acetone (30 mL) in a 100 mL round bottom flask with stirring. The reaction mixture was refluxed for 5 hrs. and then allowed to cool to room temperature. The resultant white solid was collected by filtration and dried in vacuo for 7 hrs. to yield the isopropylidine protected dopamine ribonamide (0.99 g, 2.90 mmol, 87.6% yield). $^1$H and $^{13}$C-NMR results were consistent with structure. Melting point was found to 142-143° C.

EXAMPLE 1-6

Reduction of Isopropylidine Protected Dopamide Ribonamide Yielding Dopamine Ribonamide Isopropylidine-protected dopamide ribonamide (EXAMPLE 5; 0.70 gm; 2.05 mmol) was added slowly to 1 M Borane in THF (25 mL) in a 100 mL round bottom flask with stirring. The reaction mixture was refluxed for 2 hr. and allowed to cool to room temperature. Excess solvent was removed by rotary evaporation and methanolic HCl was added to the resulting residue. The resuspended residue was refluxed for 2 hr. and solvent was then evaporated yielding a thick hygroscopic syrup (complicating melting point analysis). The syrup was dried in vacuo for 6 hrs. to give the dopamine ribonamide-HCl salt as product (0.20 gm, 0.62 mmol, 30.3% yield) $^1$H and $^{13}$C-NMR results were consistent with structure.

Synthesis of dopamine gluconamine from the dopamine gluconamide Compound #1 involved first protecting the dopamine aromatic hydroxyl groups by addition of acetone, stirring, refluxing and cooling to form the isopropylidine-protected product as a white solid. The solid was removed by filtration and dried in vacuo. Second, the dopamine gluconamide carbonyl group was reduced by addition of Borane in THF, and after refluxing, cooling, and solvent removal by rotary evaporation methanolic HCl was added and the solution was again refluxed. Solvent was removed by evaporation and the solid dopamine gluconamine product was recrystallized using a mixture of acetonitrile and ethanol. The recrystallized reduced dopamine gluconamine product (i.e., referred to below as Compound #2) was dried in vacuo.

By way of non-limiting illustration, using Applicant's methods amide and amine products were prepared e.g., for at least the following pharmaceutical agents: namely, dopamine ribonamine and ribonamide; p-aminobenzoic acid gluconamine and gluconamide; p-aminosalicyclic acid gluconamine and gluconamide; acyclovir gluconamine and gluconamide; tryptamine gluconamine and gluconamide; sulfamethoxazol gluconamine and gluconamide; sulfasalazine gluconamine and gluconamide; phenethylamine gluconamine and gluconamide; and, benzocaine gluconamine and gluconamide.

EXAMPLE 2

Ready Solution for Administration as a Measured Dose

Ready solutions for administration as a measured dose were prepared according to TABLE A, below.

TABLE A

| Component | Amount |
|---|---|
| Compound #1 or #2 | 2.5 gm |
| Methyl-p-aminobenzoic acid | 0.014 gm |
| Propyl-p-aminobenzoic acid | 0.020 gm |
| Saccharin sodium | 0.050 gm |
| Flavoring agent | 0.001 gm |
| Citric acid | 0.200 gm |

TABLE A-continued

| Component | Amount |
|---|---|
| Sodium citrate | 0.320 gm |
| Distilled water USP q.s. to | 100 ml |

EXAMPLE 3

Powder Composition for Reconstitution Prior to Use

Powder composition suitable for reconstitution before use were prepared according to TABLE B.

TABLE B

| Component | Amount |
|---|---|
| Compound #1 or #2 | 2.5 mg |
| Sodium citrate | 20.0 mg |
| Sorbitol | 2.0 mg |
| Flavoring agent | 0.1 mg |
| Distilled water USP for reconstitution | 10.0 ml |

EXAMPLE 4

Tablets for Oral Administration

Tablets for oral administration were prepared according to TABLE C.

TABLE C

| Component | Amount |
|---|---|
| Compound #1 or #2 | 250 mg |
| Starch | 17 mg |
| Sodium glycolate (starch) | 40 mg |
| Polyvinal pyrrolidene | 7.0 mg |
| Microcrystalline cellulose | 45 mg |
| Magnesium sterate | 2.0 mg |

EXAMPLE 5

Tablets for Sublingual Administration

Tablets for sublingual administration were prepared according to TABLE D.

TABLE D

| Component | Amount |
|---|---|
| Compound #1 or #2 | 250 mg |
| Gum arabic | 10 mg |
| Lactose | 90 mg |
| Ammonium glycyrrhiznate | 20 mg |
| Sodium saccharin | 2 mg |
| Flavor | 10 mg |
| Magnesium sterate | 7 mg |

EXAMPLE 6

Dopamine Receptor Binding

To illustrate biological activity, i.e., dopaminergic activity, and putative pharmaceutical utility, dopamine receptor binding activity of Compounds #1 and #2 (supra) was tested in vitro using COS-7 cells transiently transfected with pCD-PS expression vectors containing human D1, human D5 and human D2 (long) inserts, i.e., according to Materials and Methods disclosed further below. Binding to dopaminergic receptors was tested as ability to compete binding of specific receptor ligands (i.e., [$^3$H]-SCH-23390 for D1; [$^3$H]-emonapride for D2), as well as, the ability to trigger intracellular second messengers, i.e., cAMP.

Competition binding assays were initiated in duplicate with 0.5 ml aliquots of membrane preparations from cell cultures transfected with cDNA encoding human D1- or D2-receptors. Test compounds (Compounds #1 or #2, supra) were added as competitors to achieve a final concentration in the assay in the range of $10^{-4}$M to $10^{-11}$M. As binding ligand, 400 pM of [$^3$H]-SCH-23390 (a D1-selective agonist) or 150 pM of [$^3$H]-Emonapride (a D2-selective agonist) were added to each assay. After 90 minutes incubation at room temperature the assay was terminated by rapid filtration and membrane bound [$^3$H] was determined by scintillation spectrometry.

Test Compounds #1 and #2 successfully competed [$^3$H]-SCH-23390 binding to dopamine receptors in cells transiently expressing both the D1- and D5-receptors, i.e., in a dose-response and uniphasic type manner with $K_i$ values expectedly somewhat less than those recorded in parallel with natural dopamine as the control compound. Under these particular conditions of assay, the illustrative test Compounds #1 and #2 showed selectivity for D5-over D1-receptors, i.e., a property held in common with natural dopamine agonist. Under conditions of this particular assay, test Compounds #1 and #2 did not compete with binding of [$^3$H]-Emonapride at D2-receptors. Alternative assays for assessing D2-receptor functional activity of test compounds include inhibition of agonist-induced cAMP accumulation.

Agonist functional activity assays were conducted by evaluating ability of test compound to trigger production of second messengers in dopamine D1- or D5-receptor transfected COS-7 cells, i.e., cAMP. Incubation with test compound (or dopamine as a positive control) were conducted at 37° C. (5% $CO_2$) for 15 min. and cAMP accumulation was determined by radioimmunoassay. For comparison, dopamine as a positive control stimulated accumulation of cAMP by about 5-fold in D1-transfected cells and about 3-fold in D5-transfectants. In both D1- and D5-transfectants, Compound #2 stimulated cAMP accumulation in a dose-response manner to levels near those achieved in dopamine control cultures. Co-incubation of dopamine with Compound #2 did not reduce the levels of cAMP accumulation recorded, suggesting strongly that the compounds produced according to the instant methods act as agonists, not antagonists.

In summary, test Compounds #1 and #2, prepared according to the methods of the invention, exhibited relatively high affinity and agonist activity for human D5- and D-1 dopaminergic receptors. The test compounds are thus illustrative of transportable prodrug compounds that retain receptor ligand binding- and functional-activity.

EXAMPLE 7

Dopamine Transporter Binding Activity

To further illustrate biological activity, i.e., transportability within the brain, Compounds #1 and #2 (supra) dopamine transporter (DAT) binding activity of Compounds #1 and #2 was evaluated by measuring their ability to compete uptake of $^3$H-labeled dopamine by human DAT-transfected HEK 293 cells over the course of a 5 hour incubation period. To obtain differing levels of DAT expression, HEK 293 cells were transiently transfected) using calcium phosphate-mediated transfection (Maniatis et al., 1982) with 2, 5, 10, 20, 40 and 50 μg pcDNA 1.1.1 containing human dopamine transporter cDNA insert (hDAT), or alternatively, control irrelevant cDNA insert (Negative Control, NC. After 48-72 hrs. culture, dopamine transport was measured in the transiently transfected hDAT-cells by incubation for 5 hrs. in the presence of $^3$H-labeled dopamine (Positive Control, PC). In assays designed to test Compound #2, 2 μg of Compound #2 (Exptl) was added to the incubation medium. Percentage competition of dopamine uptake was calculated as follows: namely, Percentage competition =(PC—NC)-(Exptl.-NC)/(PC—NC)×100%. At 2 μg Compound #2 effectively competed $^3$H-dopamine uptake in cultures as follows: namely, at 5 μg and 10 μg hDAT cDNA, 84% competition; 20 μg hDAT cDNA, 68% competition; 40 μg hDAT cDNA, 48% competition; and, at 50 μg hDAT cDNA 68% competition. Having established Compound #2 to be capable of effectively competing with dopamine for transport by hDAT in cell cultures putatively expressing different levels of hDAT, experiments were next conducted to determine whether the competing activity exhibited dose-response characteristics. For these studies, HEK 293 cells were transfected with pcDNA1.1.1-hDAT (or control) cDNA at 40 μg and dopamine transport activity was assessed after 1 hr. or 5 hrs. of culture. Addition of Compound #1 or #2 at 2 μg or 5 μg competed with $^3$H-dopamine transport in the hDAT-transfected cells in a dose-response manner as follows: namely, at 1 hr. 2 μg or 5 μg Compound #1 gave 39% and 66% competition, respectively; and at 5 hrs. 2 μg or 5 μg of Compound #1 gave 16% and 66% competition, respectively.

To effect higher level cellular expression of dopamine transporter, liposome-mediated co-transfection methods (i.e., "InsectSelect™ Glow Kit", "Insectin®" and "InsectSelect™", Invitrogen Inc., Carlsbad, Calif.) are useful e.g., to co-transfect cells (e.g., Sf9 insect cells) with both a human dopamine transporter cDNA (cDAT) expression vector and an expression vector encoding a green fluorescent protein (GFP) reporter and a selectable marker, e.g., a Zeocin™ (Zeo) resistance gene (e.g., pIZT/V$^5$-His; GFP-Zeo). For example, methods such as those provided as the manufacturer's product recommendations (Invitrogen, supra). Transfected selected Zeo-resistant cells are selected for high level constitutive expression GFP and concomitant high level DAT expression.

Illustrative Materials and Methods

Cell Culture and Dopamine Receptor Expression: COS-7 cells were cultured at 37° C. in Dulbecco's modified Eagles medium (D-MEM) containing 10% fetal bovine serum. Human D1, human D5 and human D2 (long form) were subcloned in pCD-PS for use in the transient expression studies. COS-7 cells were transfected with either CsCl purified plasmid DNA, or Bio-101 "monster" plasmid purified by electroporation. For receptor binding studies transfected cells were cultured in 150-mm plates and for cAMP studies the transfected cells were cultured in 24 well plates.

Dopamine Receptor Binding Assays: [$^3$H]-SCH-23390 (New England Nuclear, NEN, 81.4-86.5 Ci/mmol; 1 Ci=37 GBq) and [$^3$H]-Emonapride (NEN, 68.2 Ci/mmol) were purchased. For use in binding assays membranes were prepared from 72 hr. cultures of transfected cells expressing D1 or D2, i.e., in buffer (50 mM Tris-HCl, pH 7.4, 5 mM EDTA, 1.5 mM $CaCl_2$, 5 mM KCl, 5 mM $MgCl_2$, 120 mM NaCl) by sonication (Polytron, 6/30 sec.), centrifugation (18,000 rpm/15 min.) and resuspension to a final protein concentration of 120-150 µg/ml (Bradford protein assay; Biorad Laboratories, Inc., Oakland, Calif.). Non-specific binding was determined in the presence of 10 µM (+)-butaclamol. Data were analyzed by the nonlinear least-squares fitting program KALE DAGRAPH (Abelbeck Software, Reading, Pa.).

Agonist Second Messenger Assays: COS-7 cells transiently transfected with cDNA encoding human D1- or D5-receptors were cultured for 48-72 hours in 6 or 24 well culture dishes in D-MEM containing 0.5 mM 3-isobutylmethylxanthine and 1 µM propranolol. cAMP content was measured by radioimmunoassay according to the manufacturer's instructions (Amersham).

CITATIONS

Alexander, N., Yoneda, S., Vlachakis, N.D. and R. F. Maronde. 1984. Role of conjugation and red blood cells for inactivation of circulating catecholamines. Am. J. Physiol. 247 (1): R203-R207.

Barrett, A., McQuade, R. D. and C. Tedford. 1992. Highlights of D1 dopamine receptor antagonist research. Neurochem. Int. 20 (Suppl.): 119S-122S.

Bencsics, A., Sershen, H., Baranyi, M., Hashim, A., Lajtha, A. and E. S. Vizi. 1997. dopamine, as well as norepinephrine, is a link between noradrenergic nerve terminals and splenocytes. Brain Res. 761 (2): 236-243.

Bodor et al. 1978. J. Pharm. Sci, 67 (5): 685.

Bodor, 1976. "Novel Approaches for the Design of Membrane Transport Properties of Drugs". In: "Design of Biopharmaceutical Properties Through Prodrugs and Analogs", Ed. E. B. Roche et al. APhA Academy of Pharmaceutical Sciences, Washington, D.C., pp. 98-135

Bodor et al, 1981. Science 214: 1370-1372.

Bodor et al, 1983. Pharmacology and Therapeutics 19 (3): 337-386.

Casagrande, C., Santagelo, F., Saini, C., Doggi, F., Gerli, F. and C. Cerri. 1986. Synthesis and chemical properties of Ibopamine and of related esters of N-substituted dopamines: Synthesis of Ibopamine metabolites. Arzneim. Forsch. 36 (2a): 291-303.

Chen, N., Ferrer, J. V., Havitch, J. A. and J. B. Justice. 2000. Transport-dependent accessibility of a cytoplasmic loop cysteine in human dopamine transporter. J. Biol. Chem. 275 (3): 1608-1614.

Choi, S. W., Elmaleh, D. R., Hanson, R. N. and A. J. Fishman. 2000. Novel 3-aminomethyl- and 4-aminopiperidine analogues of 1-[2-(diphenylmethoxy)ethyl]-4-(3-phenylpropyl)piperazines: Synthesis and evaluation as dopamine transporter ligands. J. Med. Chem. 43 (2): 205-213.

Clarkson, E. D., Edwards-Prasad, J., Freed, C. R. and K. N. Prasad. 1999. Immortalized dpamine neurons: A model to study neurotoxicity and neuroprotection. Proc. Soc. Exp. Biol. Med. 222 (2): 157-163.

Claustre, J., Pequignot, J. M., Bui-Xuan, B., Muchada, R., Cottet-Emard, R. M. and L. Peyrin. 1990. Conjugation and deamination of circulating dopamine: Relationship between sulfated and free dopamine in man. J. Auton, Nerv. Syst. 29 (2): 175-182.

Coffey, L. L. and M. Reith. 1994. [$^3$H]WIN 35,428 binding to the dopamine uptake carrier. I. Effect of tonicity and buffer composition. J. Neurosci. Methods 51 (1): 23-30.

Diez-Sampedro, A., Urdaneta, E., Lostao, M. P. and A. Barber. 1999. Galactose transport inhibition by cytochalasin E in rat intestine in vitro. Can. J. Physiol. Pharmacol. 77 (2): 96-101.

Duport, S., Robert, F., Muller, D., Grau, G., Parisi, L. and L. Stoppini. 1998. An in vitro blood-brain barrier model: Cocultures between endothelial cells and organotypic brain slice cultures. Proc. Natl. Acad. Sci. USA 95 (4): 1840-1845.

Earles, C. and J. O, Shenk. 1999. Multisubstrate mechanism for the inward transport of dopamine by the human dopamine transporter expressed in HEK cells and its inhibition by cocaine. Synapse 33 (3): 230-238.

Figlewicz, D. P. 1999. Endocrine regulation of neurotransmitter transporters. Epilepsy Res. 37 (3): 203-210.

Findlay, J., Levy, G. A. and C. A. Marsh. 1958. Inhibition of glycosidases by aldonolactones or corresponding configuration. 2. Inhibitors of β-N-acetylglucosaminidase. Biochemical J. 69: 467-476.

Fischer, Y., Thomas, Y., Kamp, J., Juengling, E., Rose, H., Carpen, C. and H. Kammermeier. 1995. 5-Hydroxytraptamine stimulates glucose transport in cardiomyocytes via a monoamine oxidase-dependent reaction. Biochem. J. 311 (2): 575-583.

Fodor et al. 1961. Acta Chim. Acad. Sci. Hung. 28 (4): 409.

Gee, J. M., DuPont, M. S., Rhodes, M. J. and I. T. Johnson. 1998. Quercetin glucosides interact with the intestinal glucose transporter pathway. Free Radic. Biol. Med. 25 (1): 19-25.

Gerding, T. K., Drenth, B. F. H., DeZeeuw, R. A., Tepper, P. G. and A. S. Horn. 1990. Metabolism and disposition of the dopamine agonist 2-(N-propyl-N-2-thienylethylamino)-5-hydroxytetraline in conscious monkeys after subsequent iv, oral and ocular administration. Drug. Metab. Dispos. 18 (6): 923-928.

Geurts, M., Hermans, E. and J. M. Maloteaux. 1999. Assessment of striatal D1 and D2 dopamine receptor-G protein coupling by agonist-induced [$^{35}$S]GTP gamma S binding. Life Sci. 65 (16): 1633-1645.

Gainetdinov, R. R., Jones, S. R. and M. G. Caron. 1999. Functional hyperdopaminergia in dopamine transporter knock-out mice. Biol. Psychiatry 46 (3): 303-311.

Giros, B., el Mestikawy, S., Bertrand, L. and M. G. Caron. 1991. Cloning and functional characterization of a cocaine-sensitive dopamine transporter. FEBS Lett. 295: 149-154.

Giros, B., el Mestikawy, S., Godinot, N., Zheng, K., Han, H., Yang-Feng, T. and M. G. Caron. 1992. Cloning, pharmacological characterization and chromosome assignment of the human dopamine transporter. Mol. Pharmacol. 42 (3): 383-390.

Green, M. D. and T. R. Tephly. 1996. Glucuronidation of amines and hydroxylated xenobiotics and endobiotics catalyzed by expressed human UGT1.4 protein. Drug Metab. Dispos. 24 (3): 356-363.

Haspel, H. C., Stephenson, K. N., Davies-Hill, T., El-Barbary, A., Lobo, J. F., Croxen, R. L., Mougrabi, W., Koehler-Stec, E. M., Fenstermacher, J. D. and I. A. Simpson. 1999. Effects of barbiturates on facilitative glucose transporters are pharmacologically specific and isoform selective. J. Membr. Biol. 169 (1): 45-53.

Horton, D. 1969. Monosaccharide Amino Sugars. In: "The Amino Sugars": The Chemistry and Biology of Compounds Containing Amino Sugars. Vol. 1A. Ed. R. W. Jeanloz. Academic Press, N.Y. pp. 4-18.

Huang, X., Xu, R., Hawley, M. D., Hopkins, T. L. and K. J. Kramer. 1998. Electrochemical oxidation of N-acyldopamines and regioselective reactions of their quinones with N-acetylcysteine and thiourea. Arch. Biochem. Biophys. 352 (1): 19-30.

Husbands, et al., 1999. Structure-activity relationships at the monoamine transporters as sigma receptors for a novel series of 9-[3-(cis,5-dimethyl-1-piperazinyl)propyl]carbazole (rmicazole) analogues. J. Med. Chem. 42 (21): 4446-4455.

Hyson, D. H., Thomson, A. B. and C. T. Kappagoda. 1996. Calcium channel blockers modify jejunal uptake of D-galactose in rabbits. Dig. Dis. Sci. 41 (9): 1871-1875.

Hyson, D. H., Thomson, A. B., Keelan, M. and C. T. Kappagoda. 1997. A high cholesterol diet blocks the effect of calcium channel blockers on the uptake of sugars in rabbit intestine. Can. J. Physiol. Pharmacol. 75 (1): 57-64.

Jaber, M., Dumartin, B., Sagne, C., Haycock, J. W., Roubert, C., Giros, B., Bloch, B. and M. G. Caron. 1999. Differential regulation of tyrosine hydroxylase in the basal ganglion of micre lacking the dopamine transporter. Eur. J. Neurosci. 11 (10): 3499-3511.

Jones, S. R., Joseph, J. D., Barak, L. S., Caron, M. G. and R. M. Wightman. 1999. Dopamine neuronal transport kinetics and effects of amphetamine. J. Neurochem. 73 (6): 2406-2414.

Jork, R., Lossner, B. and H. Matthies. 1980. The influence of dopamine on the incorporation of different sugars into total proteins of hippocampal slices. Pharmacol. Biochem. Behav. 13 (2): 303-304.

Kawasaki, H. and M. Yago. 1983. The identification of two N-acyldopamine glucosides in the left colleterial gland of the praying mantid, Tenodera aridifolia sinensis Saussure, and their role in the oothecal sclerotization. Insect Biochem. 13: 267-271.

Kerwin, J. L. 1996. Negative ion electrospray mass spectrometry of polyphenols, catecholamines and their oxidation products. J. Mass Sprectrom. 31: 1429-1439.

Kerwin, J. L. 1997. Profiling peptide adducts of oxidized N-acetyldopamine by electrospray mass spectrometry. Rapid Commun. Mass Sprectrom. 11: 557-566.

Kerwin, J. L., Whitney, D. L. and A. Sheikh. 1999. Mass spectrometry of glucosamine, glucosamine polymers and their catecholamine adducts. Model reactions and cuticular hydrolysates of Toxorhynchites amboinensis (Culicidae) pupae. Insect Biochem. Mol. Biol. 29 (7): 599-607.

Kikuchi, T., Tottori, K., Uwahodo, Y., Hirose, T., Miwa, T., Oshiro, Y. and S. Morita. 1995. 7-(4-[4-(2,3-Dichlorophenyl)-1-piperazinyl]butyloxy)-3,4-dihydro-2(1H)-quinolinone(OPC14597) a new antipsychotic drug with both presynaptic dopamine autoreceptoragonist activity and post-synaptic D2 receptorantagonistic activity. J. Pharmacol. Exp. Ther. 274: 329-336.

Kilbourn, M. R., Kuszpit, K. and P. Sherman. 2000. Rapid and differentiallosses of in vivo dopamine transporter (DAT) and vesicular monoamine transporter (VMAT2) radioligand binding in MPTP-treated mice. Synapse 35 (4): 250-255.

Kilty, J. E., Lorang, D. and S. G. Amara. 1991. Cloning and expression of a cocaine-sensitive rat dopamine transporter. Science 254 (5031): 578-579.

Kuchel, O. 1999. Peripheral dopamine in hypertension and associated conditions. J. Hum. Hypertens. 13 (9): 605-615.

Kumagai, A. K. 1999. Glucose transport in brain and retina: Implications in the management and complications of diabetes. Diabetes Metab. Res. Rev. 15 (4): 261-273.

Lawler, C. P., Prioleau, C., Lewis, M. M., Mak, C., Jiang, D., Schetz, J. A., Gonzalez, A. M., Sibley, D. R. and R. B. Mailman. 1999. Interactions of the novel antipsychotic aripiprazole (OP C14597) with dopamine and sertonin receptor subtypes. Neuropsychopharm. 20(6): 612-627.

Leal, M., Hayes, M. J. and M. L. Powell. 1992. The metabolism of CGS15873 in man using stable isotope pattern recognition techniques. Biopharm. Drug Dispos. 13 (8): 617-628.

Lostao, M. P., Urdaneta, E., Martinez-Anso, E., Barber, A. and J. A. Martinez. 1998. Presence of leptin receptors in rat small intestine and leptin effect on sugar absorption. FEBS Lett. 423 (3): 302-306.

Loland, C. J., Norregaard, L. and U. Gether. 1999. Defining proximity relationships in the tertiary structure of the dopamine transporter. Identification of a conserved glutamic acid third coordinate in the endogenous $Zn^{2+}$ binding site. J. Biol. Chem. 274: 36928-36934.

Maniatis, T., Fritsch, E. F. and J. Sambrook. 1982. Molecular Cloning: A Laboratory Manual. Cold Springs Harbor Press.

Manzi, A. E. and A. Varki. 1993. In: Glycobiology: A Practical Approach. Eds. M. Fukuda and A. Kobata. lin Press, Oxford University, Oxford. pp 29-31.

Martin, M. G., Turk, E., Lostao, M. P., Kerner, C. and E. M. Wright. 1996. Defects in $Na^+$/glucose cotransporter (SGLT1) trafficking and function cause glucose-galactose malabsorption. Nat. Genet. 12 (2): 216-220.

Mattiuz, E., Freanklin, R., Gillespie, T., Murphy, A., Bernstein, J., Chiur, A., Hotten, T. and K. Kassahun. 1997. Disposition and metabolism of olanzapine in mice, dogs and rhesus monkeys. Drug Metab. Dispos. 25 (5): 573-583.

Melikian, H. E. and K. M. Buckley. 1999. Membrane trafficking regulates the activity of the human dopamine transporter. J. Neurosci. 19 (18): 7699-7710.

Meyer, W., Buehring, K. U., Steiner, K., Ungethum, W. and E. Schnurr. 1992. Pharmacokinetics and first clinical experiences with an antihypertensive dopamine (DA2) agonist. Eur. Heart J. 13 (Suppl. D): 121-128.

Mico, B. A., Swagzdis, J. E., Federowicz, D. A. and K. Straub. 1986. Function-group metabolism of dopamine-2 agonists: Conversion of 4-(2-di-N-propylamnoethyl)-2-($^3$H)-indolone to 4-(2-di-N-propylaminoethyl)-7-hydroxyl-2-($^3$H)-indolone. J. Pharm. Sci. 75 (10): 929-933.

Miller, G. W., Gainetdinov, R. R., Levey, A. I. and M. G. Caron. 1999. Dopamine transporters and neuronal injury. Trends Phramacol. Sci. 20(10): 424-429.

Mizuma, T., Ohta, K. and S. Awazu. 1994. The beta-anomeric and glucose preferences of glucose transport carrier for intestinal active absorption of monosaccharide conjugates. Biochim. Biophys. Acta 1200 (2): 117-122.

Morgan, T. D., Hopkins, T. L., Kramer, K. J., Roseland, C. R., Czapala, T. H., Tomer, K. B. and Crow, F. W. 1987. N-β-Alanylnorepinephrine: Biosynthesis in insect cuticle and possible role in sclerotization. Insect Biochem. 17: 255-263.

Morgan, M. J. and K. B. Franklin. 1991. Dopamine receptor subtypes and formalin test analgesia. Pharmacol. Biochem. Behav. 40 (2): 317-322.

Mueller, D. D., Morgan, T. D., Wassenberg, J. D., Hopkins, T. L. and K. J. Kramer. 1993. 1H and 13C NMR of 3-O and 4-O conjugates of dopamine and other catecholamines. Bioconjug. Chem. 4(1): 47-53.

Navarro, H., Arruebo, M. P., Alcalde, A. I. and V. Sorribas. 1993. Effect of erythromycin on D-galactose absorption and sucrase activity in rabbit jejunum. Can. J. Physiol. Pharmacol. 71 (3-4): 191-194.

Pokorski, M. and Z. Matysiak. 1998. Fatty acid acylation of dopamine in the carotid body. Med. Hypothesis. 50 (2): 131-133.

Pocchiari, F., Pataccini, R., Castelnovo, P., Longo, A. and C. Casagrande. 1986. Ibopamine, an orally active dopamine-like drug: Metabolism and pharmacokinetics in rats. Arzneim.-Forsch. 36 (2A): 334-340.

Prakash, C., Cui, D., Baxter, J. G., Bright, G. M., Miceli, J. and K. Wilner. 1998. Metabolism and excretion of a new anxiolytic drug candidate, CP-93,393, in healthy male volunteers. Drug Metab. Dispos. 26 (5): 448-456.

Prakash, K. R., Tamiz, A. P., Araldi, G. L., Zhang, M., Johnson, K. M. and A. Kozikowski. 1999. N-phenylalkyl-substituted tropane analogs of boat conformation of high selectivity for the dopamine versus serotonin transporter. Bioorg. Med. Chem. Lett. 9 (23): 3325-3328.

Rhoads, D. B., Rosenbaum, D. H., Unsal, H., Isselbacher, K. J. and L. L. Levitsky. 1998. Circadian periodicity of intestinal $Na^+$/glucose cotransporter 1 mRNA levels is transcriptionally regulated. J. Biol. Chem. 273 (16): 9510-9516.

Schauer, R. 1978. In: Methods in Enzymology, Ed. V. Ginsberg. Academic Press, NY. pp. 64-89.

Shimada, S., Kitayama, S., Lin, C. L., Patel, A., Nanthakumar, E., Gregor, P., Kuhar, M. and G. Uhl. 1991. Cloning and expression of a cocaine-sensitive dopamine transporter complementary DNA. Science 254 (5031): 576-578.

Shindo, H., Komai, T. and K. Kawai. 1973. Metabolism of D- and L-isomers of 3,4 dihydroxyphenylalanine (DOPA). V. Mechanism of intestinal absorption of carbon-14 labeled D- and L-dopa in rats. Chem. Pharm. Bull 21 (9): 2031-2038.

Storch, A., Ludolph, A. C. and J. Schwarz. 1999. HEK-293 cells expressing the human dopamine transporter are susceptible to low concentrations of 1-methyl-4-phenylpuridine acting via impairment of energy metabolism. Neurochem. Int. 35 (5): 393-403.

Sugamori, K. S., Lee, F. J., Pristupa, Z. B. and H. B. Niznik,. 1999. A cognate dopamine transporter-like activity endogenously expressed in a COS-7 kidney derived cell line. FEBS Lett. 451 (2): 169-174.

Sugumaran, M. 1991. Molecular mechanisms from mammalian melanogenesis. Comparison with insect cuticular sclerotization. FEBS Lett. 295 (1-3): 233-239.

Sugumaran, M. and E. Nelson. 1998. Model sclerotization studies. 4. Generation of N-acetylmethionyl catechol adducts during tyrosinase-catalyzed oxidation of catechols in the presence of N-acetylmethionine. Arch. Insect. Biochem. Physiol. 38 (1): 44-52.

Umegae, Y., H. Nohta and Y. Ohkura. 1988. Anal. Chim. Acta 208: 59.

Vandenbergh, D. J., Persico, A. M. and G. R. Uhl. 1992. A human dopamine transporter cDNA predicts reduced glycosylation, displays a novel repetitive element and provides racially-dimorphic TaqI RFLPs. Brain Res. Mol. Brain. Res. 15 (1-2): 161-166.

Vannucci, S. J., Clark, R. R., Koehler-Stec, E., Li, K., Smith, C. B., Davies, P., Maher, F. and I. A. Simpson. 1998. Glucose transporter expression in brain: Relationship to cerebral glucose utilization. Dev. Neurosci. 20 (4-5): 369-379.

Verhoeff, N. P. 1999. Radiotracer imaging of dopaminergic transmission in neuropsychiatric disorders. Psychopharmacol. (Berl) 147 (3): 217-249.

Wang, P. C., Nguyen, T. B., Kuchel, O. and J. Genest. 1983. Conjugation patterns of endogenous plasma catecholamines in human and rat. J. Lab. Clin. Med. 101 (1): 141-151.

Wang, P. C., Kuchel, O., Buu, N. T. and J. Genest. 1983. Cathecholamine glucuronidation: An important metabolic pathway for dopamine in the rat. J. Neurochem. 40 (5): 1435-1440.

Whitfield, C. F., Rannels, S. R. and H. E. Morgan. 1974. Acceleration of sugar transport in avian erythrocytes by catecholamines. J. Biol. Chem. 249 (13): 4181-4188.

Wright, E. M., Hirsch, J. R., Loo, D. D. and G. A. Zampighi. 1997. Regulation of $Na^+$/glucose cotransporters. J. Exp. Biol. 200 (2): 287-293.

Wu, X. and H. H. Gu. 1999. Molecular cloning of the mouse dopamine transporter and pharmacological comparison with the human homologue. Gene 233 (1): 163-170.

Wybrandt, G. B. and S. O. Andersen. 1994. Cuticle-catalyzed coupling between polyamino acids and N-acetyldopamine. Biochim. Biophys. Acta 1201 (1): 15-18.

Yago et al. 1988. The identification of fiber N-Acyldopamine glucosides in the left colleterial gland of the praying mantid. Insect. Biochem. 14 (5): 487-489.

Yasuda, Y., Kikuchi, T., Suzuki, S., Tsutsui, M., Yamada, K. and T. Hiyama. 1988. 7-[3-(4-[2,3-dimethyl-phenyl]piper-azinyl)propoxy]-2(1H)-quinolinone (OPC04392), a presynaptic dopamine autoreceptor agonist and postsynaptic D2 receptor antagonist. Life Sci. 42:1941-1954.

While the preferred embodiment of the invention has been illustrated and described, it will be appreciated that various changes can be made therein without departing from the spirit and scope of the invention.

What is claimed is:

1. A method for ameliorating Parkinson's Disease in a subject in need thereof, comprising administering to the subject a pharmaceutical composition comprising a compound according to FORMULA I:

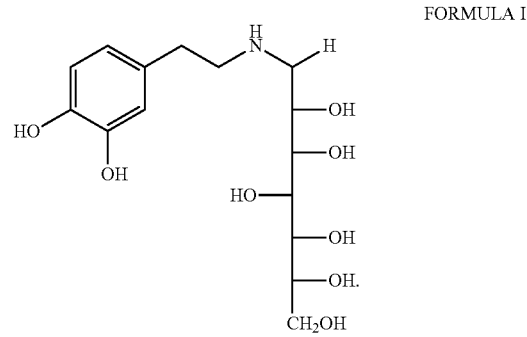 [SMILES: OCC(O)C(O)C(O)C(O)C(O)CNCCc1ccc(O)c(O)c1]

FORMULA I

2. The method of claim 1, wherein the pharmaceutical composition further comprises an agent selected from the group consisting of an additive, a stabilizer, a carrier, a binder, a buffer, an excipient, an emollient, a disintegrant, a lubricating agent, an antimicrobial agent and a preservative.

* * * * *